(12) United States Patent
Newman et al.

(10) Patent No.: US 11,891,723 B2
(45) Date of Patent: Feb. 6, 2024

(54) SYSTEM AND PROCESS FOR PREPARING A FIBROUS NONWOVEN COMPOSITE FABRIC

(71) Applicant: Fitesa Simpsonville, Inc., Simpsonville, SC (US)

(72) Inventors: Marc Newman, Simpsonville, SC (US); Rene Ruschel, Greer, SC (US); Yu Xin, Greer, SC (US)

(73) Assignee: Fitesa Simpsonville, Inc., Simpsonville, SC (US)

( * ) Notice: Subject to any disclaimer, the term of this patent is extended or adjusted under 35 U.S.C. 154(b) by 0 days.

(21) Appl. No.: 17/740,044

(22) Filed: May 9, 2022

(65) Prior Publication Data

US 2022/0372655 A1    Nov. 24, 2022

Related U.S. Application Data

(60) Provisional application No. 63/242,058, filed on Sep. 9, 2021, provisional application No. 63/186,176, filed on May 9, 2021.

(51) Int. Cl.
*D01D 5/08* (2006.01)
*D01D 5/088* (2006.01)
(Continued)

(52) U.S. Cl.
CPC .......... *D01D 4/02* (2013.01); *A61F 13/15658* (2013.01); *D01D 4/025* (2013.01);
(Continued)

(58) Field of Classification Search
CPC ...... A61F 13/15658; A61F 2013/15934; A61F 2013/15943; A61F 2013/15959;
(Continued)

(56) References Cited

U.S. PATENT DOCUMENTS 4,380,570 A * 4/1983 Schwarz .............. D01D 5/0985
442/350
5,476,616 A * 12/1995 Schwarz .............. D01D 5/0985
425/72.2 X (Continued)

FOREIGN PATENT DOCUMENTS

CN    104775171 A    7/2015
CN    111534866 A    8/2020
(Continued)

OTHER PUBLICATIONS

International Search Report for International Application No. PCT/US2022/028362, dated Aug. 25, 2022 (4 pages).

(Continued)

*Primary Examiner* — Leo B Tentoni

(57) ABSTRACT

A system having a first polymer source and a spin beam in fluid communication with the first polymer source is provided. The spin beam includes a spinneret assembly having filament nozzles configured and arranged to extrude a plurality of filaments of a first polymer. A gas distribution plate is disposed downstream of the spinneret assembly, and includes a plurality of gas distribution slots that are configured and arranged to receive two or more corresponding filament nozzles of the spinneret assembly therein. A stream of gas is introduced into the plurality of slots to draw and attenuate the filaments extruded by the plurality of filament nozzles. The drawn and attenuated filaments are collected on a collection surface disposed downstream of the gas distribution plate to form a nonwoven fabric. A solid additive, such as pulp fibers may be blended with the filaments prior to collecting the filaments on the collection surface.

19 Claims, 30 Drawing Sheets
(17 of 30 Drawing Sheet(s) Filed in Color)

(51) Int. Cl.
*D01D 5/30* (2006.01)
*D01D 13/00* (2006.01)
*D01D 13/02* (2006.01)
*D04H 1/26* (2012.01)
*D04H 1/407* (2012.01)
*D04H 3/005* (2012.01)
*D04H 5/00* (2012.01)
*D01D 4/02* (2006.01)
*D01D 7/00* (2006.01)
*D04H 3/015* (2012.01)
*D04H 3/033* (2012.01)
*A61F 13/15* (2006.01)
*D04H 1/4382* (2012.01)
*D01D 5/098* (2006.01)

(52) U.S. Cl.
CPC ............. *D01D 5/0985* (2013.01); *D01D 7/00* (2013.01); *D04H 1/43835* (2020.05); *D04H 3/015* (2013.01); *D04H 3/033* (2013.01); *A61F 2013/15934* (2013.01); *A61F 2013/15943* (2013.01); *A61F 2013/15959* (2013.01); *A61F 2013/15967* (2013.01)

(58) Field of Classification Search
CPC ............ A61F 2013/15967; D01D 4/02; D01D 4/025; D01D 5/08; D01D 5/088; D01D 5/0985; D01D 5/30; D01D 7/00; D01D 13/00; D01D 13/02; D04H 1/26; D04H 1/407; D04H 1/43835; D04H 3/005; D04H 5/00

USPC .......... 264/103, 121, 131, 211.12, 330, 518, 264/555; 425/72.2, 83.1, 131.5, 133.1, 425/224, 377, 382.2, 464; 19/296, 299
See application file for complete search history.

(56) References Cited

U.S. PATENT DOCUMENTS

| | | | |
|---|---|---|---|
| 5,618,566 A * | 4/1997 | Allen ................... | D01D 5/0985 425/464 |
| 5,948,710 A * | 9/1999 | Pomplun ................. | D04H 5/00 442/341 |
| 5,952,251 A | 9/1999 | Jackson | |
| 2003/0038409 A1 | 2/2003 | Allen | |
| 2005/0233021 A1 | 10/2005 | Chun et al. | |
| 2009/0023839 A1* | 1/2009 | Barnholtz ............ | D01D 5/0985 523/222 |

FOREIGN PATENT DOCUMENTS

| | | |
|---|---|---|
| DE | 202008015313 U1 | 6/2009 |
| WO | 2020099193 A1 | 5/2020 |

OTHER PUBLICATIONS

Written Opinion of the International Searching Authority for International Application No. PCT/US2022/028362, dated Aug. 25, 2022 (8 pages).

* cited by examiner

SYSTEM AND PROCESS FOR PREPARING A FIBROUS NONWOVEN COMPOSITE FABRIC

This application claims the benefit of priority to U.S. Provisional Application No. 63/242,058, filed on Sep. 9, 2021, and U.S. Provisional Application No. 63/186,176, filed May 9, 2021, the contents of which are both hereby incorporated by reference in their entirety.

FIELD

The presently disclosed invention relates generally to nonwoven fabrics, and more particularly to a system and process for preparing a fibrous nonwoven composite material.

BACKGROUND

Fibrous nonwoven materials and fibrous nonwoven composite materials are widely used in disposable wipers. Several methods are used for producing these fibrous nonwoven materials. In one approach, called airlaid, cellulosic fibers are bonded together into a web using an adhesive emulsion. This web must be dried to remove the water and set the adhesive. The resulting web tends to be stiff, due to the presence of the adhesive that binds the fibers.

Another approach, called spunlacing, employs jets of high velocity water to mechanically interlock the fibers in the web. This process commonly uses staple fibers and wood fibers as components in the web. Continuous filaments produced by the spunbond process can also be combined with wood fibers in the spunlacing process. Because adhesive is not commonly used in the spunlacing process, the fibers have substantial freedom to bend and twist, and the resulting webs are soft and drapeable. However, synthetic; fibers are significantly more expensive than wood fibers and the spunlacing process has high capital and operating costs.

A third approach used to prepare absorbent nonwovens is to form a blend of absorbent fibers and synthetic fibers produced by the meltblowing process. This type of pulp-polymer integrated composite, called coform, consists of an air formed matrix comprising meltblown microfibers having an average diameter of less than 10 microns, and a multiplicity of individualized absorbent fibers such as, for example, wood pulp fibers, disposed throughout the matrix of polymer microfibers and engaging at least some of the microfibers to space the microfibers apart from each other. The absorbent fibers are interconnected by and held captive within the matrix of microfibers by mechanical entanglement of the microfibers with the absorbent fibers, the mechanical entanglement and interconnection of the microfibers and absorbent fibers alone forming a coherent integrated fibrous structure. These materials are prepared according to the descriptions in U.S. Pat. No. 4,100,324 to Anderson et al. Patents describing the use of coform nonwoven materials and composite fabrics incorporating coform layers include U.S. Pat. Nos. 4,663,220; 4,784,892; 4,906,513; 5,952,251; 6,028,018; 6,946,413 and U.S. Patent Publication Application No. U.S. 2005/0266760A1. Generally, coform nonwovens have demonstrated good absorbency properties and have been successfully used in the manufacture of absorbent wipes.

Despite the advantageous properties of many commercially available coform nonwoven materials, there still exist a need to develop fibrous nonwoven composite materials having improved absorbency and mechanical properties, such as strength.

SUMMARY

Embodiments of the invention are directed to a process and system for preparing a nonwoven fabric comprising fine continuous or semi-continuous filaments.

In certain embodiments a system for preparing a nonwoven fabric is provided in which the system comprises a first polymer source and a spin beam in fluid communication with the first polymer source. Molten polymer from the first polymer source is provided to the spin beam. The spin beam comprises a spinneret assembly having a plurality of filament nozzles arranged in an array. The plurality of filament nozzles are configured and arranged to extrude a plurality of filaments comprising the first polymer source. A gas distribution plate is disposed downstream of the spinneret assembly. The gas distribution plate includes a plurality of gas distribution slots that are configured and arranged to receive two or more corresponding filament nozzles of the spinneret assembly therein. A gas source is in fluid communication with the plurality of gas distribution slots such that a stream of gas is introduced into the plurality of slots to draw and attenuate the filaments extruded by the plurality of filament nozzles. The drawn and attenuated filaments then are discharged through distal end of the gas distribution slots and are collected on a collection surface disposed downstream of the gas distribution plate to form a nonwoven fabric.

In certain embodiments of the system, the plurality of gas distribution slots are configured and arranged to receive a corresponding row of filament nozzles of the spinneret assembly therein.

In some embodiments of the system, the plurality of gas distribution slots are disposed adjacent to a corresponding row of filament nozzles. In certain embodiments, each individual row of filament nozzles is disposed between two rows of gas distribution slots.

In certain embodiments of the system, the spin beam comprises a pattern of alternating rows of filament nozzles and gas distribution slots. In some embodiments, the pattern of alternating rows of filament nozzles and gas distribution slots ends and begins with a gas distribution slot such that each row of filaments nozzles is disposed between a pair of gas distribution slots.

In certain embodiments of the system, the gas distribution plate comprises four side edges defining a generally rectangular shape, and wherein a gas distribution slot is disposed adjacent to each of said four side edges.

In some embodiments, each row of filament nozzles includes a plurality of segmented gas distribution slots in which at least two filament nozzles are disposed in each segmented gas distribution slot. In certain embodiments, each segmented gas distribution slot includes 2 to 100 filament nozzles disposed therein, such as embodiments in which each segmented gas distribution slot includes 4 to 10 filament nozzles disposed therein.

In certain embodiments, the segmented gas distribution slots have a rectangular, square, oval, bar bell, dog bone or butterfly shape. In one such embodiment, the segmented gas distribution slots have a bar bell shape comprising a first chamber and a second chamber that are interconnected via a fluid channel, and wherein each chamber includes at least one filament nozzle disposed therein. In some embodiments, each chamber of the segmented gas distribution slot includes 2 to 4 filament nozzles disposed therein.

In certain embodiments, the segmented gas distribution slots have a dog bone or butterfly shape comprising four interconnected lobes, wherein each lobe includes at least one filament nozzle disposed therein.

In certain embodiments, the gas distribution plate includes a plurality of filament apertures arranged in rows, wherein each aperture is configured to receive a single filament nozzle therein, a plurality gas distribution outlets arranged in rows, wherein the rows of filament apertures and rows gas distribution outlets define a pattern of alternating rows of filament nozzles and gas distribution outlets such that each gas distribution outlet is associated with at least two filament nozzles.

In certain embodiments, the pattern of alternating rows of filament nozzles and gas distribution outlets is disposed between a pair of opposing gas distribution slots.

In certain embodiments, the gas distribution plate comprises four peripheral edges defining an outer perimeter of the gas distribution plate, wherein a gas distribution slot is disposed adjacent to each of said four peripheral edges of said gas distribution plate.

In some embodiments, the plurality of gas distribution slots extend in a cross direction of the spin beam. In certain other embodiments, the plurality of gas distribution slots extend in a machine direction of the spin beam.

In some embodiments, the plurality of filament nozzles extend at least partially through a thickness of the gas distribution plate. In certain embodiments, the plurality of filament nozzles extend outwardly below a lower surface of the gas distribution plate.

In some embodiments, the plurality of filament nozzles are releasably attached to the spinneret assembly. In other embodiments, the plurality of filament nozzles are an integral part of the spinneret assembly.

In certain embodiments, the gas distribution slots have a pair of opposing side walls extending along a length of each of the gas distribution slots, and wherein the rows of filament nozzles are disposed between the pair of opposing side walls. In some embodiments, an angle formed between the opposing sidewalls and sidewalls of the filament nozzles is from 0° to 60°. In one embodiment, an angle formed between the opposing sidewalls and sidewalls of the filament nozzles is greater than 30°.

In certain embodiments, the sidewalls of the filament nozzles and the sidewalls of the gas distribution slot are parallel or substantially parallel to each other.

In some embodiments, the filament nozzles have a distal end having a generally conical shape.

In certain embodiments, the system further comprises a second polymer source for providing a second polymer to the spin beam, wherein the spin beam is configured and arranged to produce multicomponent filaments. In some embodiments, the system is configured to produce bicomponent filaments.

In some embodiments of the system, the first polymer and the second polymer are the same polymer. In certain embodiments, the first polymer and the second polymer are different polymers. In an example of a system in which the system is configured to produce multicomponent filaments, the first polymer and the second polymer comprise a polyolefin, such as polypropylene, polyethylene, and bio-based polyethylene, and copolymers thereof, polyesters, such as polyethylene terephthalate (PET), polytrimethylene terephthalate (PTT), and polybutylene terephthalate (PBT), nylons, polystyrenes, polyurethanes, aliphatic polyester based polymers, such as polylactic acid, and copolymers, and blends thereof.

In certain embodiments, the system further comprises a source of solid additives, wherein the solid additives are introduced into a stream of plurality of filaments extruded from the spin beam prior to collection of the filaments on the collection surface. In some embodiments, the source of solid additives comprises cellulose pulps, natural fibers, or a combination thereof.

In one embodiment, the solid additive comprises a cellulose pulp comprising a pulp selected from the group consisting of kraft pulp, sulfite pulp, bamboo pulp, and thermomechanical pulp.

In certain embodiments, the source of solid additives comprises a super absorbent polymer. In some embodiments, the source of solid additives comprises molecular and/or gas filters, such as zeolites, ion-exchange particles, activated carbon, and the like.

In addition, embodiments of the invention are also directed to a method of preparing a nonwoven fabric. In certain embodiments, the method comprises the steps of:
providing a first polymer source;
introducing a first polymer from said first polymer source into a spin beam in fluid communication with the first polymer source, the spin beam including a spinneret assembly having a plurality of rows of filament nozzles that are arranged in an array and a gas distribution plate disposed downstream of the spinneret assembly, the gas distribution plate including a plurality of gas distribution slots that are each associated with one or more of the rows of the filaments nozzles;
extruding a plurality of filaments comprising the first polymer provided by the first polymer source;
surrounding the filament nozzles and the extruded plurality of filaments with a stream of gas that is introduced into the plurality of gas distribution slots;
drawing and attenuating the plurality of filaments extruded by the plurality of filament nozzles; and
depositing the plurality filament nozzles onto a collection surface disposed downstream of the gas distribution plate to form a nonwoven fabric web.

In certain embodiments, the method may also comprise bonding the filaments following deposition on the collection surface. Types of bonding include thermal, mechanical and chemical bonding methods. In some embodiments, the filaments may be thermally bonded via calender bonding, air-through bonding, UV bonding and combinations thereof.

In certain embodiments of the method, the gas distribution slots may be segmented or non segmented. In some embodiments, the gas distribution slots may have a rectangular, square, oval, dumb-bell, tear drop, or butterfly shape.

In certain embodiments of the method, the plurality of gas distribution slots are configured and arranged to receive a corresponding row of filament nozzles of the spinneret assembly therein.

In some embodiments of the method, the plurality of gas distribution slots are disposed adjacent to a corresponding row of filament nozzles.

In certain embodiments of the method, each individual row of filament nozzles is disposed between two rows of gas distribution slots.

In certain embodiments of the method, the spin beam comprises an alternating of pattern of rows of filament nozzles and gas distribution slots. In some such embodiments, the pattern of alternating rows of filament nozzles and gas distribution slots ends and begins with a gas distribution slot such that each row of filaments nozzles is disposed between a pair of gas distribution slots.

In certain embodiments of the method, the gas distribution plate comprises four side edges defining a generally rectangular shape, and wherein a gas distribution slot is disposed adjacent to each of said four side edges.

In some embodiments of the method, each row of filament nozzles includes a plurality of segmented gas distribution slots in which at least two filament nozzles are disposed in each segmented gas distribution slot. In certain embodiments, each segmented gas distribution slot includes 2 to 100 filament nozzles disposed therein, such as from about 4 to 10 filament nozzles disposed therein.

In certain embodiments of the method, the segmented gas distribution slots have a rectangular, square, oval, bar bell, or butterfly shape.

In some embodiments of the method, the gas distribution slots are segments and have a bar bell shape comprising a first chamber and a second chamber that are interconnected via a fluid channel, and wherein each chamber includes at least one filament nozzle disposed therein. In some embodiments, each chamber includes 2 to 4 filament nozzles disposed therein.

In certain embodiments of the method, the gas distribution slots are segmented and have a dog bone shape comprising four interconnected lobes, wherein each lobe includes at least one filament nozzle disposed therein.

In certain embodiments of the method, the gas distribution plate includes a plurality of filament apertures arranged in rows, each aperture configured to receive a single filament nozzle therein, a plurality gas distribution outlets arranged in rows, the rows of filament apertures and rows gas distribution outlets define a pattern of alternating rows of filament nozzles and gas distribution outlets such that each gas distribution outlet is associated with at least two filament nozzles. In some embodiments, the pattern of alternating rows of filament nozzles and gas distribution outlets is disposed between a pair of opposing gas distribution slots.

In certain embodiments of the method, the gas distribution plate comprises four peripheral edges defining an outer perimeter of the gas distribution plate, wherein a gas distribution slot is disposed adjacent to each of said four peripheral edges of said gas distribution plate.

In certain embodiments of the method, the plurality of gas distribution slots extend in a cross direction of the spin beam. In certain embodiments of the method, the plurality of gas distribution slots extend in a machine direction of the spin beam.

In some embodiments of the method, the plurality of filament nozzles extend at least partially through a thickness of the gas distribution plate. In certain embodiments of the method, the plurality of filament nozzles extend outwardly below a lower surface of the gas distribution plate.

In certain embodiments of the method, the plurality of filament nozzles are releasably attached to the spinneret assembly.

In certain embodiments of the method, the gas distribution slots have a pair of opposing side walls extending along a length of each of the gas distribution slots, and wherein the rows of filament nozzles are disposed between the pair of opposing side walls. In some embodiments of the method, an angle formed between the opposing sidewalls and sidewalls of the filament nozzles is from 0° to 60°, such as an angle that is greater than 30°.

In certain embodiments of the method, the sidewalls of the filament nozzles and the sidewalls of the gas distribution slot are parallel or substantially parallel to each other.

In certain embodiments of the method, the filament nozzles have a distal end having a generally conical shape.

In certain embodiments of the method, the method may include providing a second polymer source that is in fluid communication with the spin beam. In some embodiments, the method includes preparing multicomponent filaments, such as bicomponent filaments.

In certain embodiments of the method of the method, the spin beam is configured to preparing multicomponent filaments, such as bicomponent filaments, from a first and second polymer. In some embodiments the first polymer and the second polymer are the same polymer or may be different polymers. In certain embodiments, the first polymer and the second polymer comprise a polyolefin, such as polypropylene, polyethylene, and bio-based polyethylene, and copolymers thereof, polyesters, such as polyethylene terephthalate (PET), polytrimethylene terephthalate (PIT), and polybutylene terephthalate (PBT), nylons, polystyrenes, polyurethanes, aliphatic polyester based polymers, such as polylactic acid, and copolymers, and blends thereof.

In certain embodiments, the method further comprises introducing a stream of solid additives into the plurality of filaments prior to the plurality of filaments being deposited onto the collection surface. In some embodiments, the solid additives comprises cellulose pulps, natural fibers, or a combination thereof. In certain embodiments, the cellulose pulp comprises a pulp selected from the group consisting of kraft pulp, sulfite pulp, and thermo-mechanical pulp. In some embodiments, the cellulose pulp comprises bamboo pulp.

In certain embodiments of the method, the solid additives comprise a super absorbent polymer. In some embodiments, the solid additives may comprise molecular and/or gas filters, such as zeolites, ion-exchange particles, activated carbon, and the like.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
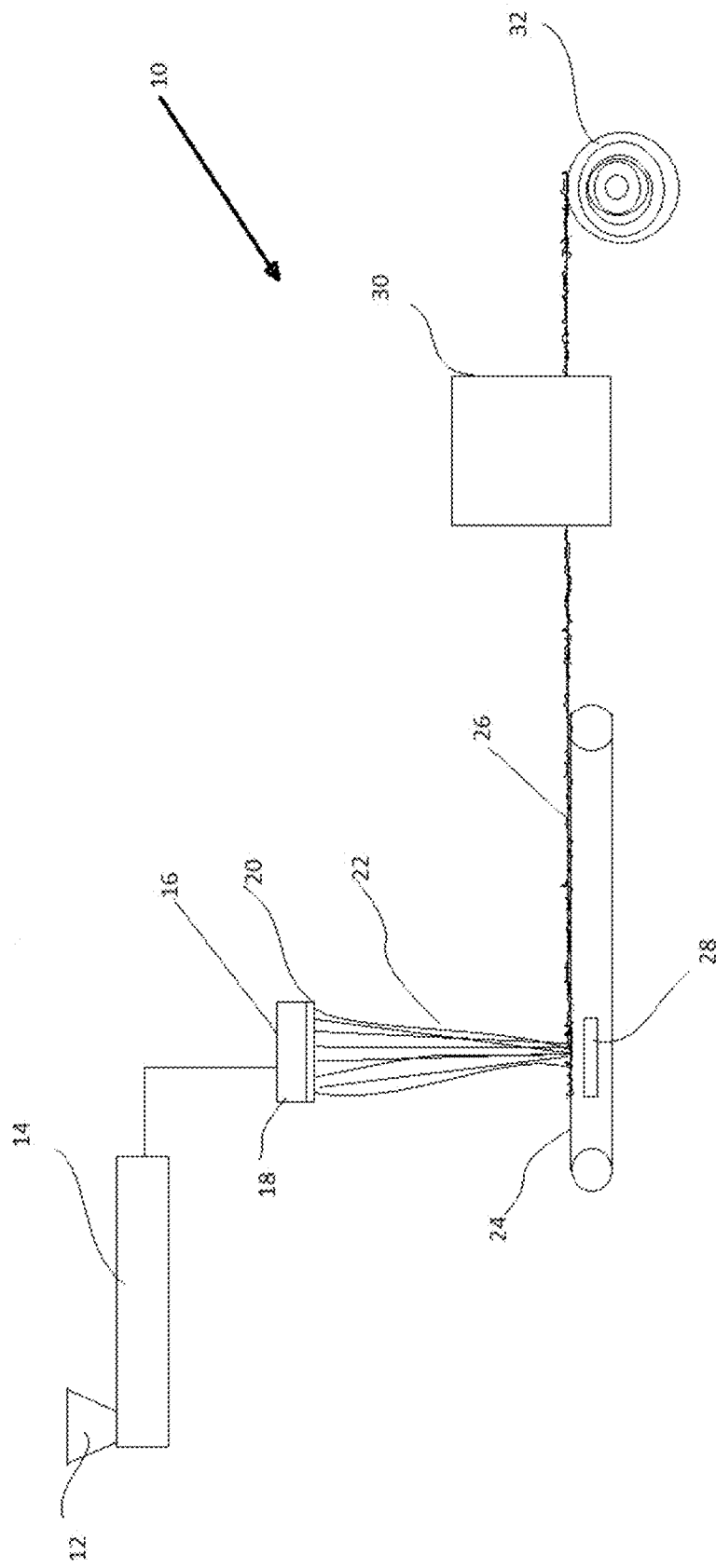
Figure 2:
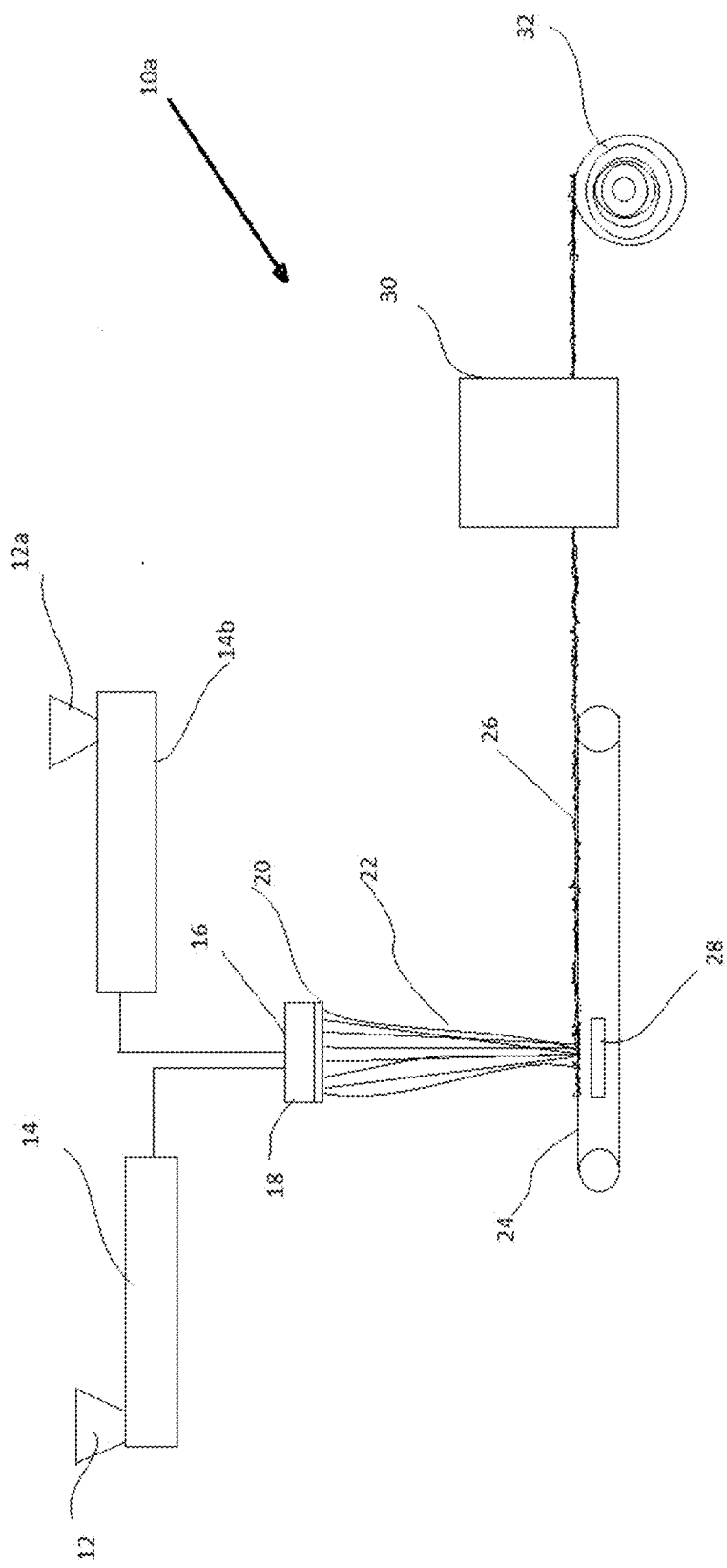
Figure 3:
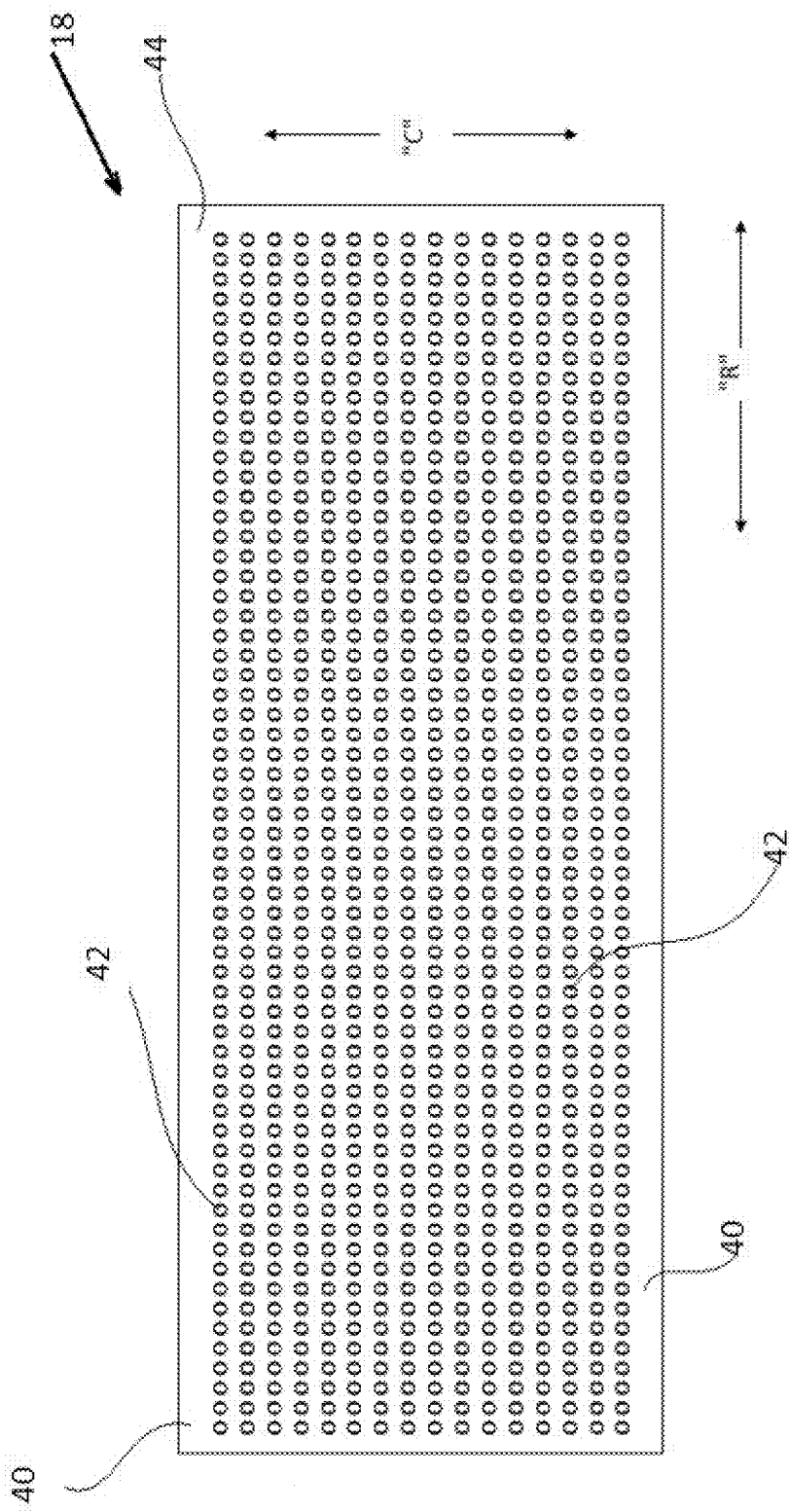
Figure 4:
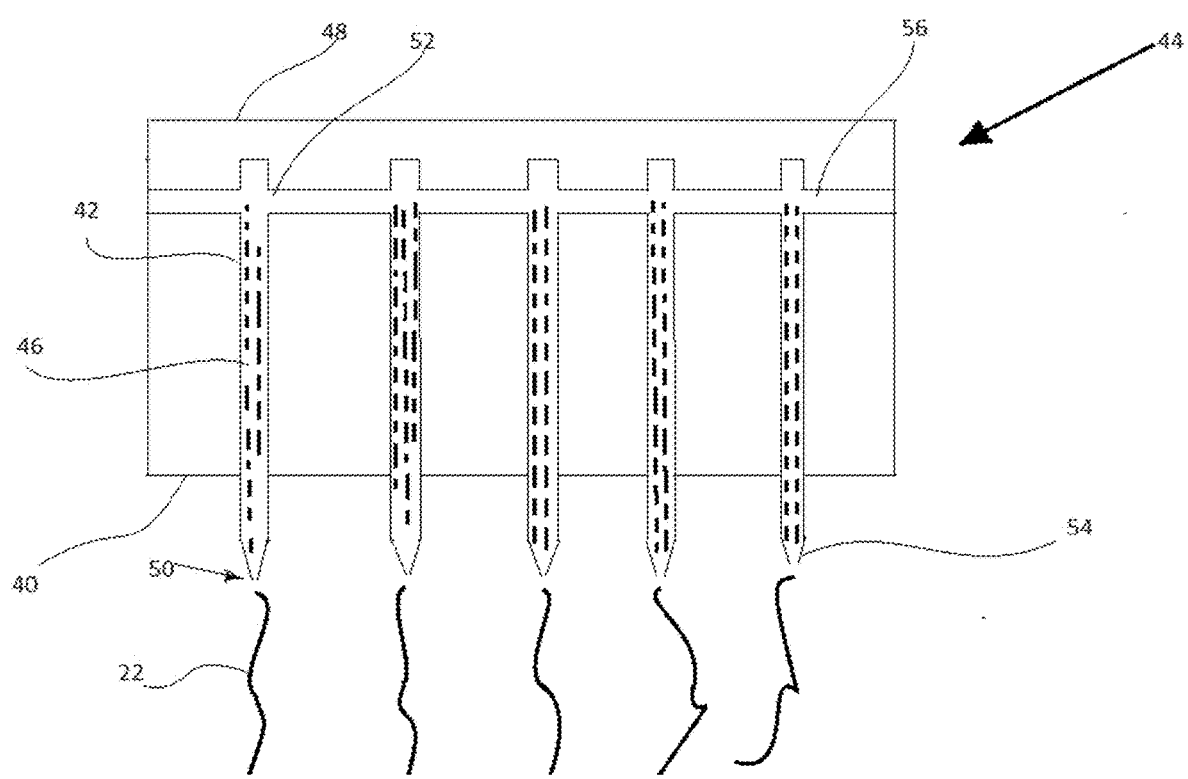
Figure 5A:
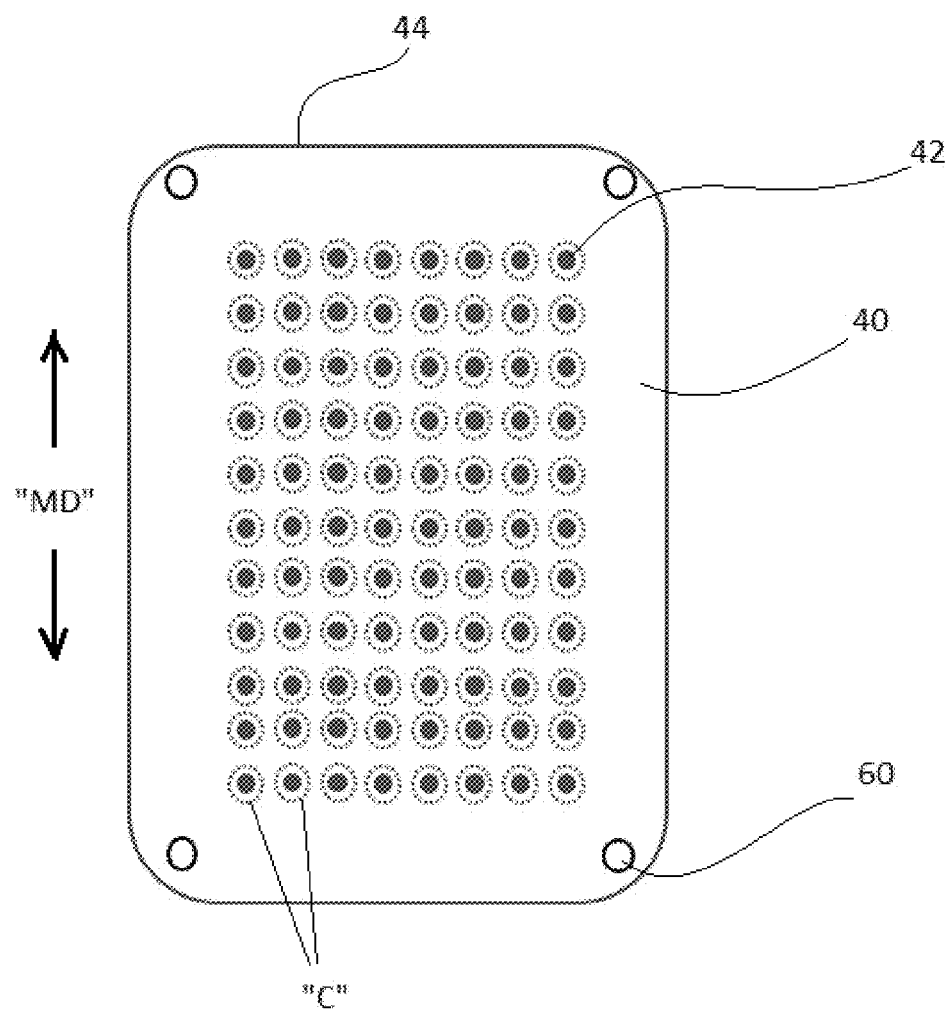
Figure 5B:
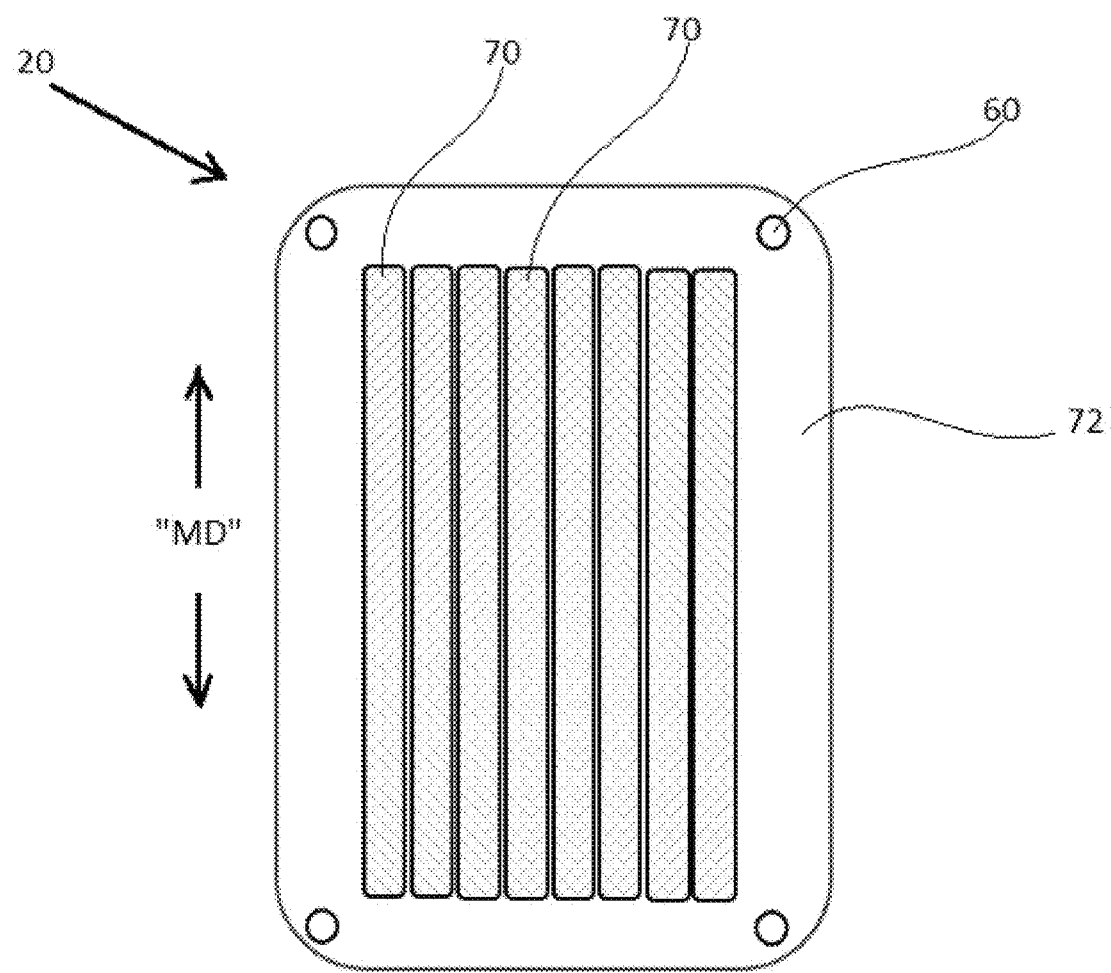
Figure 5C:
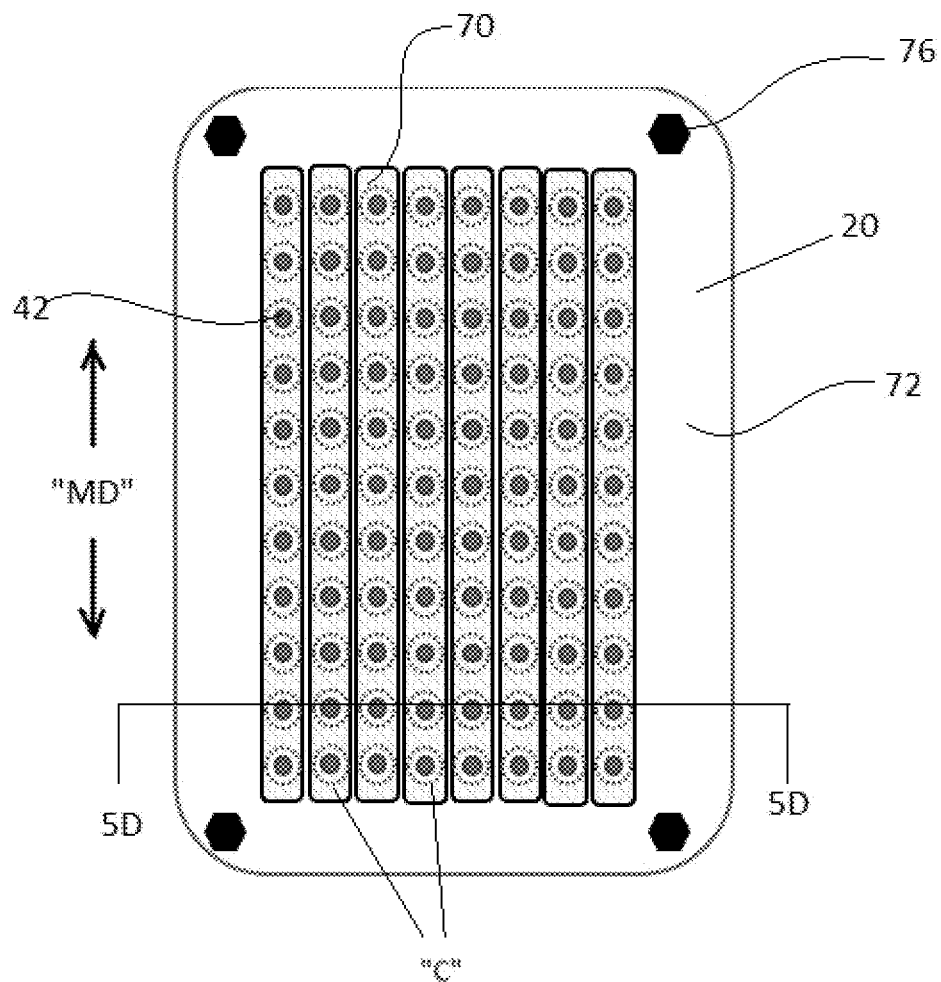
Figure 5D:
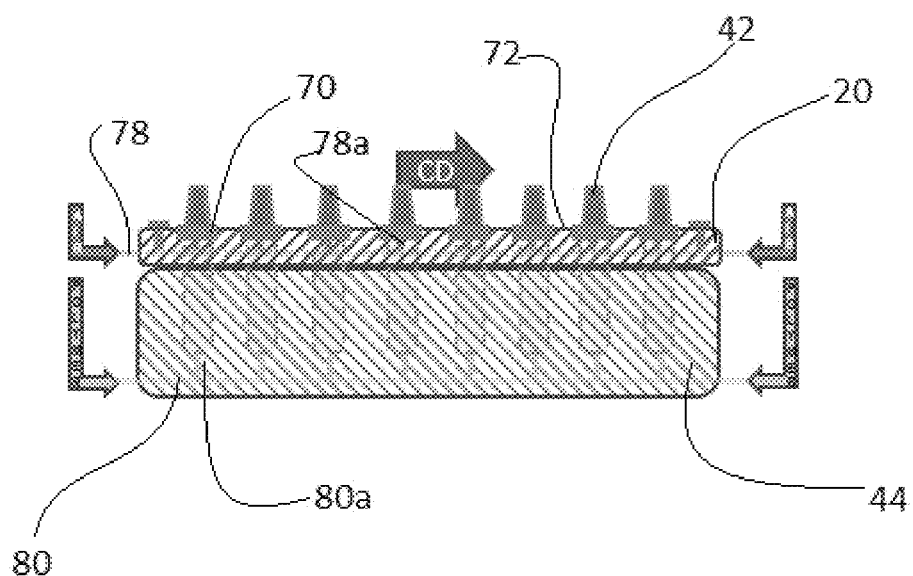
Figure 6A:
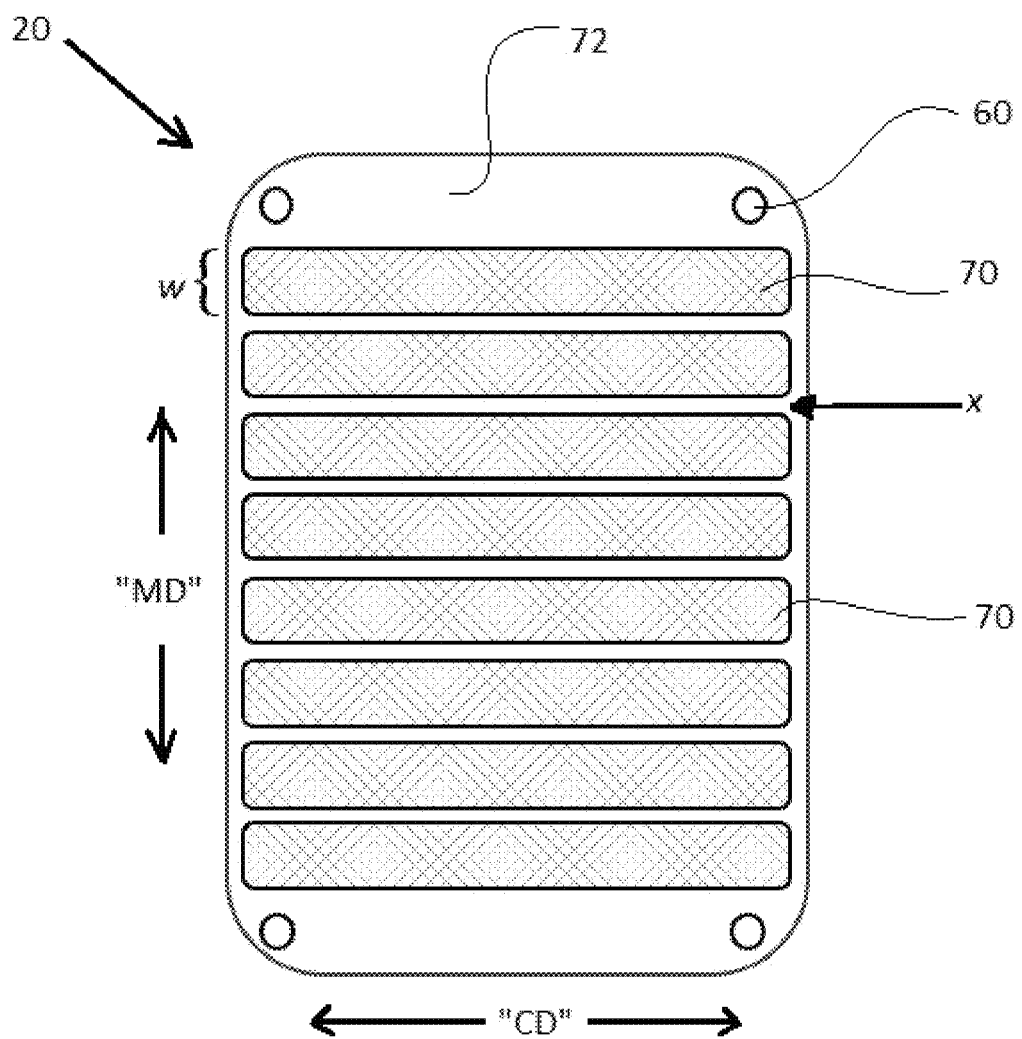
Figure 6B:
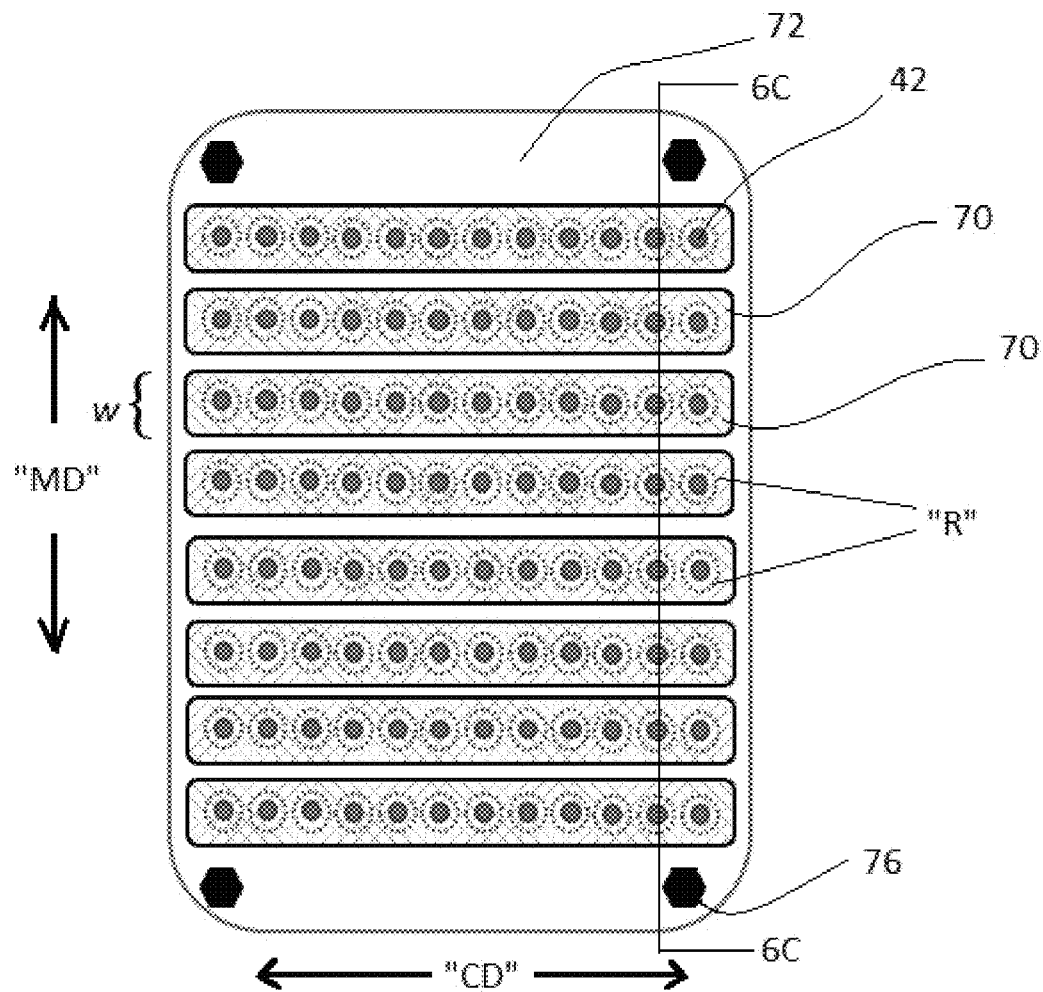
Figure 6C:
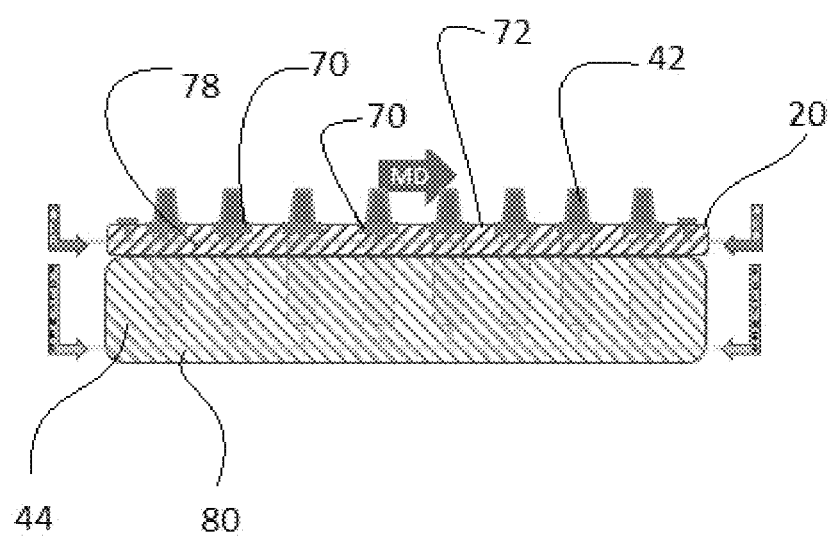
Figure 7A:
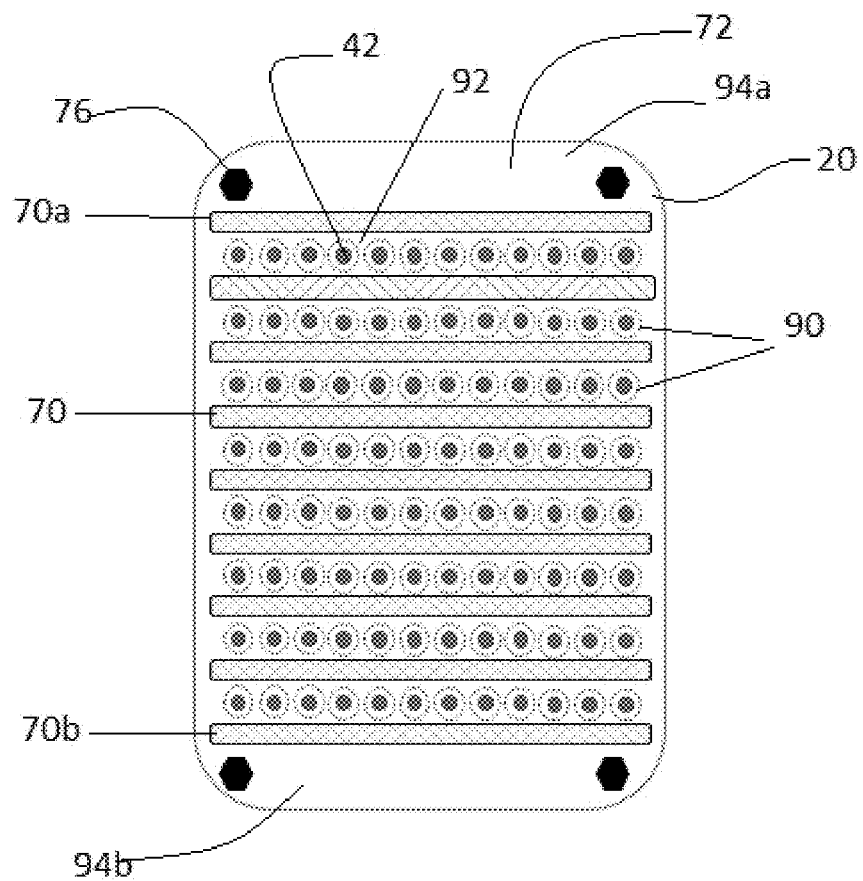
Figure 7B:
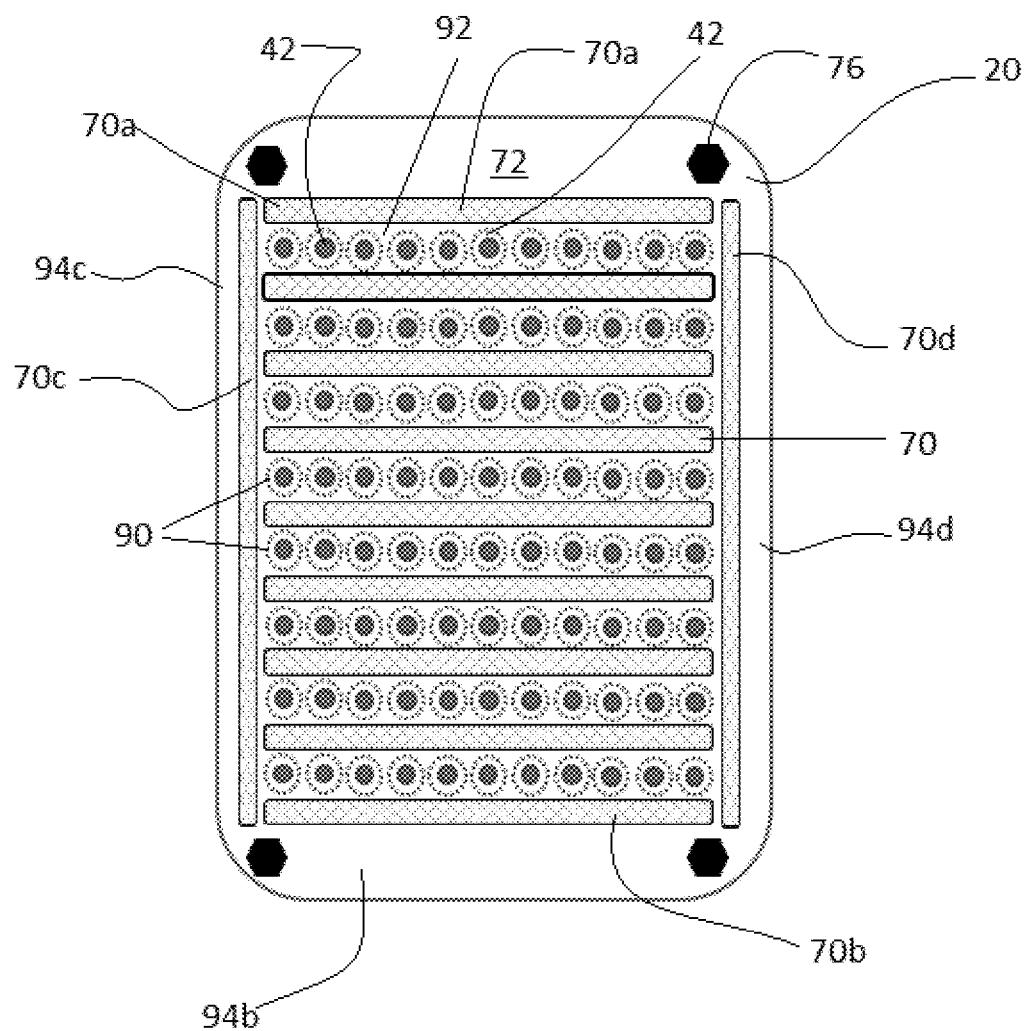
Figure 9A:
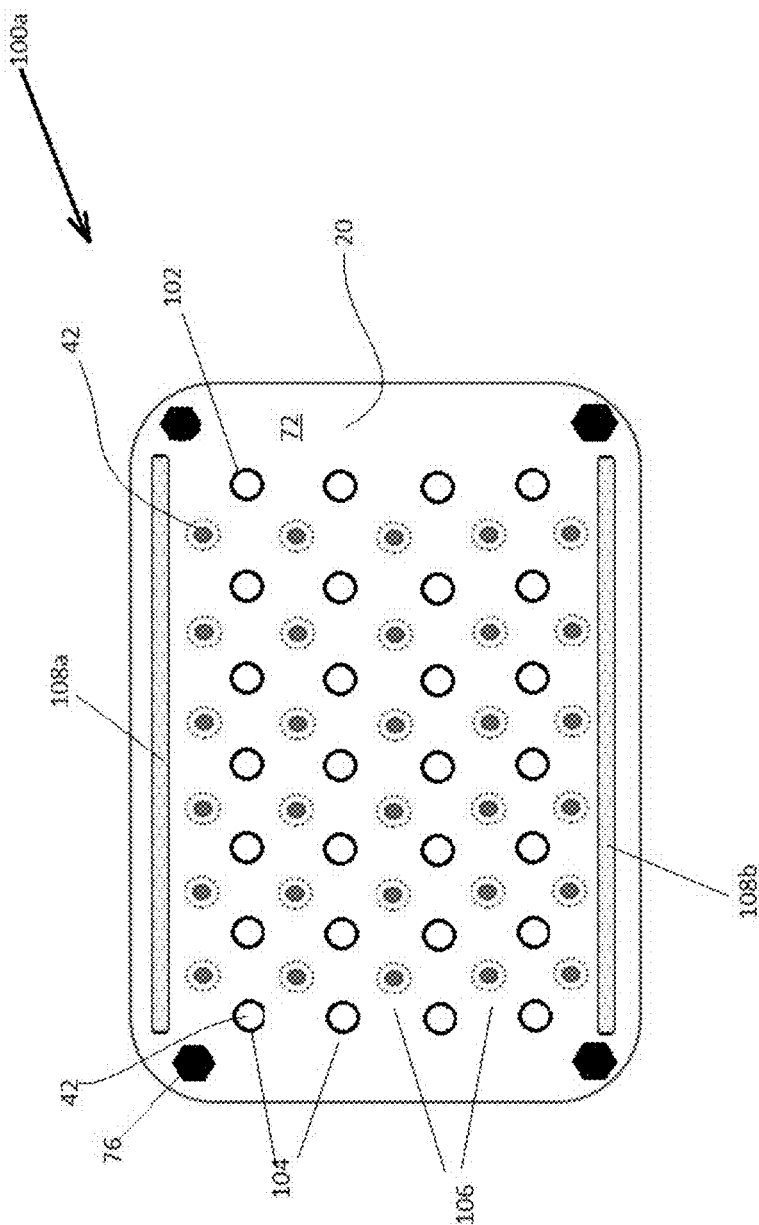
Figure 9B:
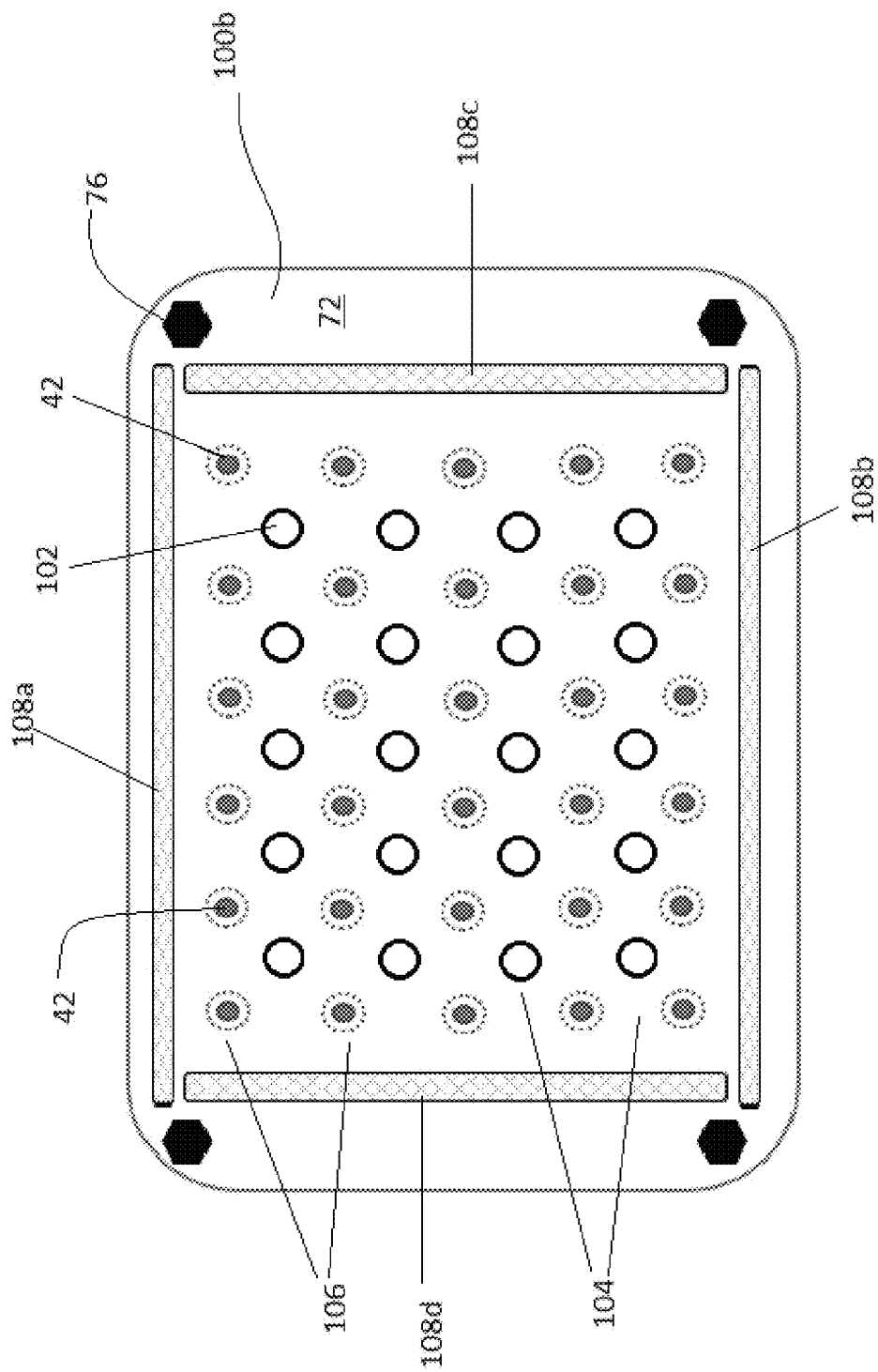
Figure 10:
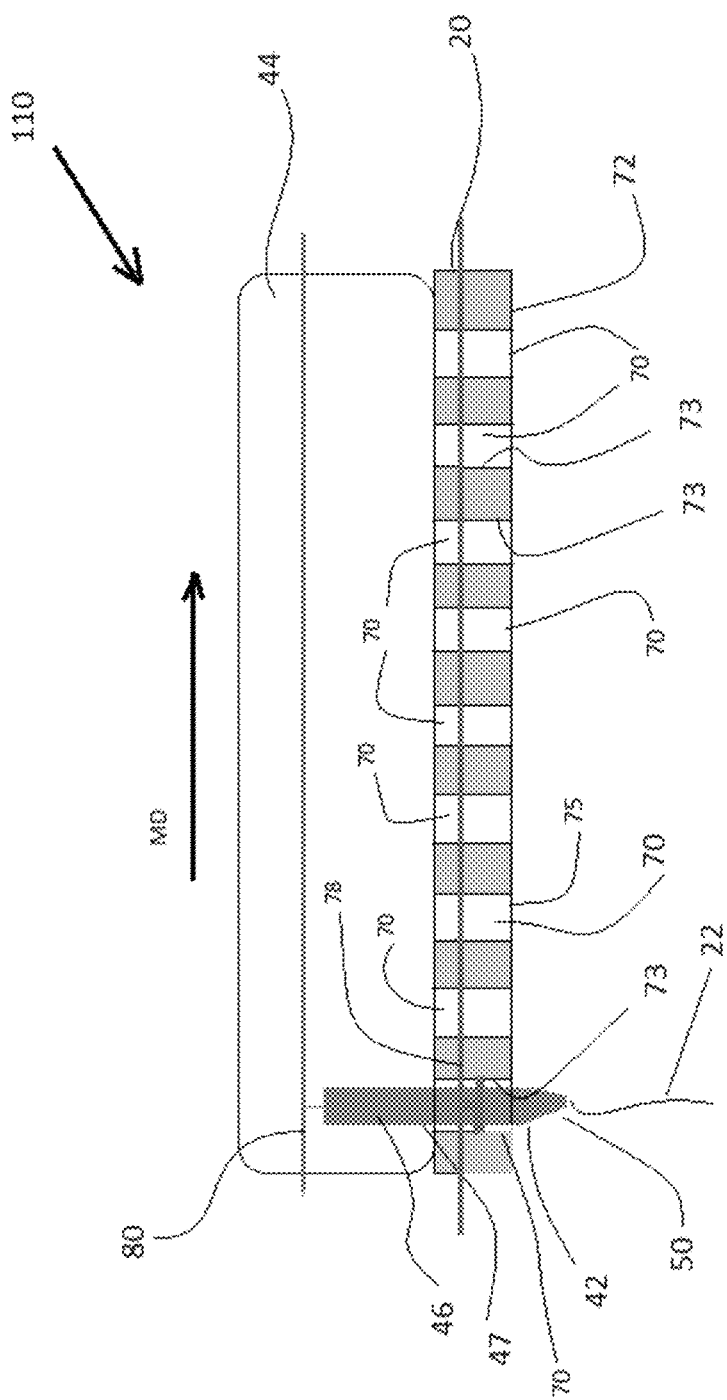
Figure 11A:
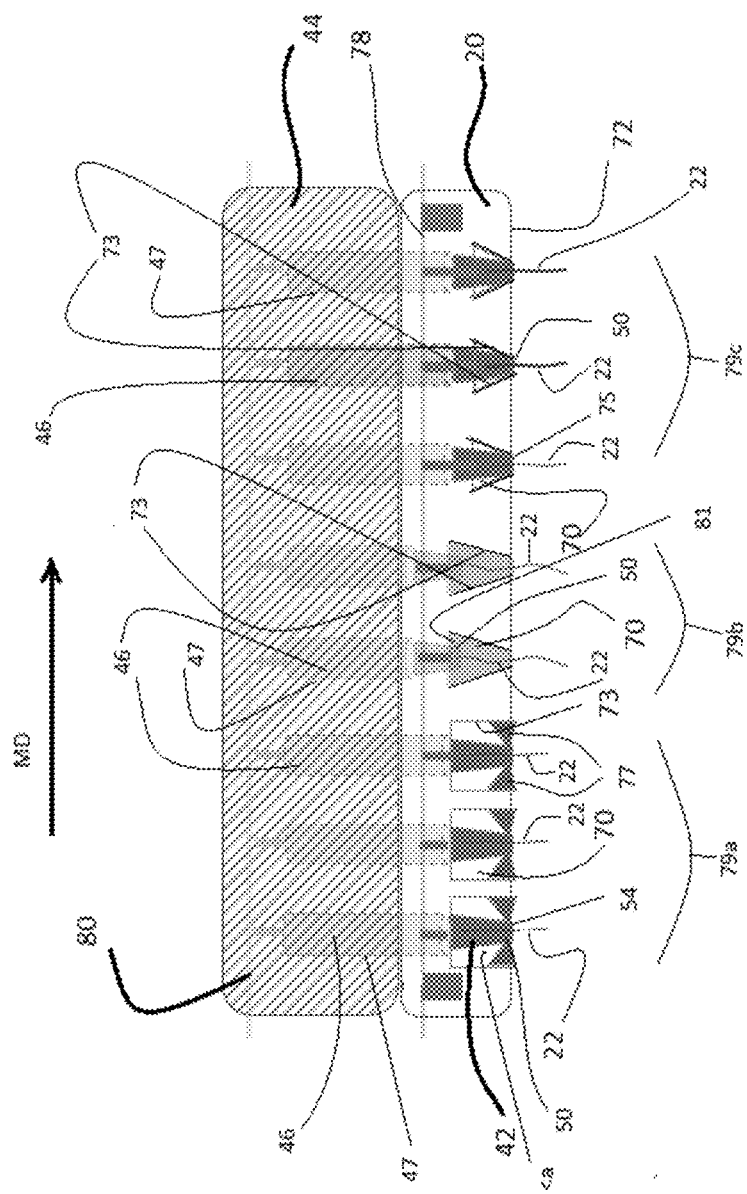
Figure 11B:
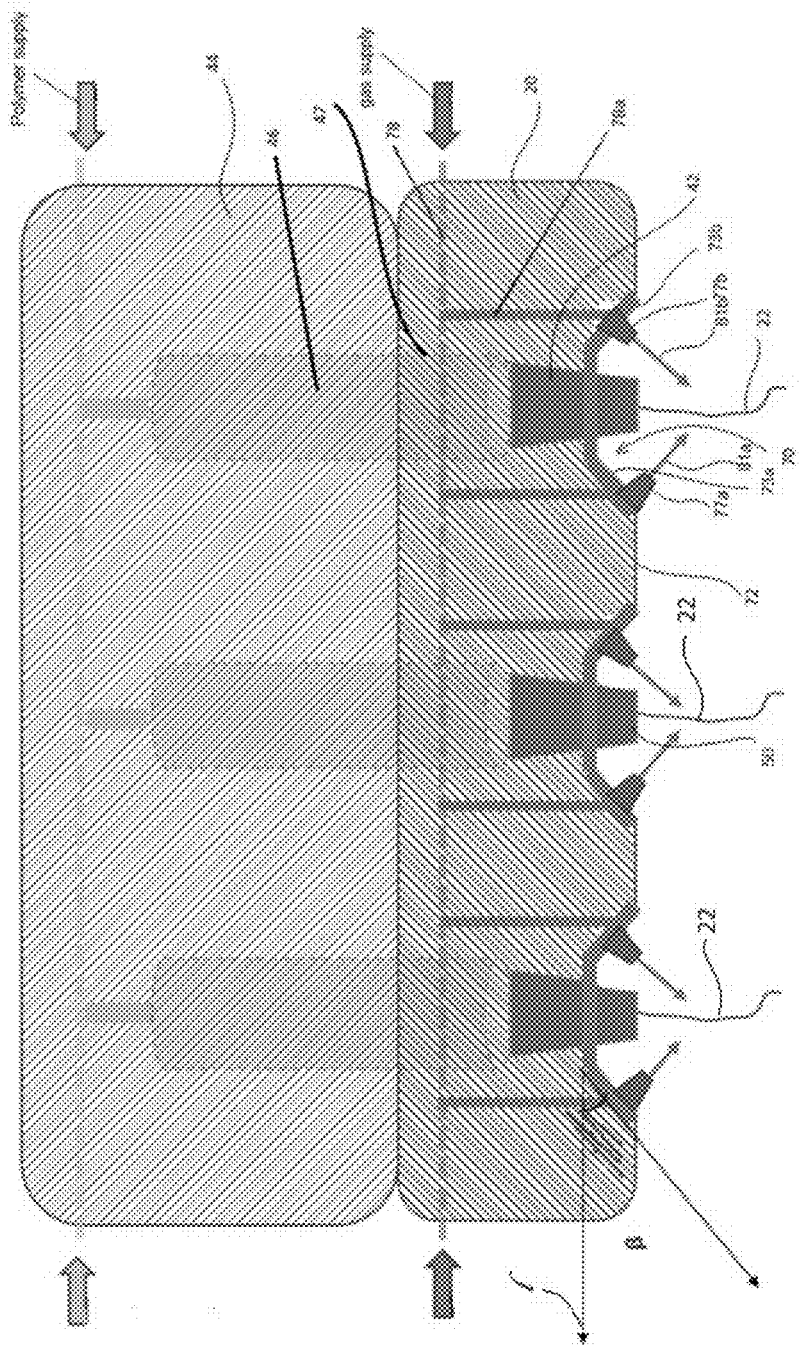
Figure 12A:
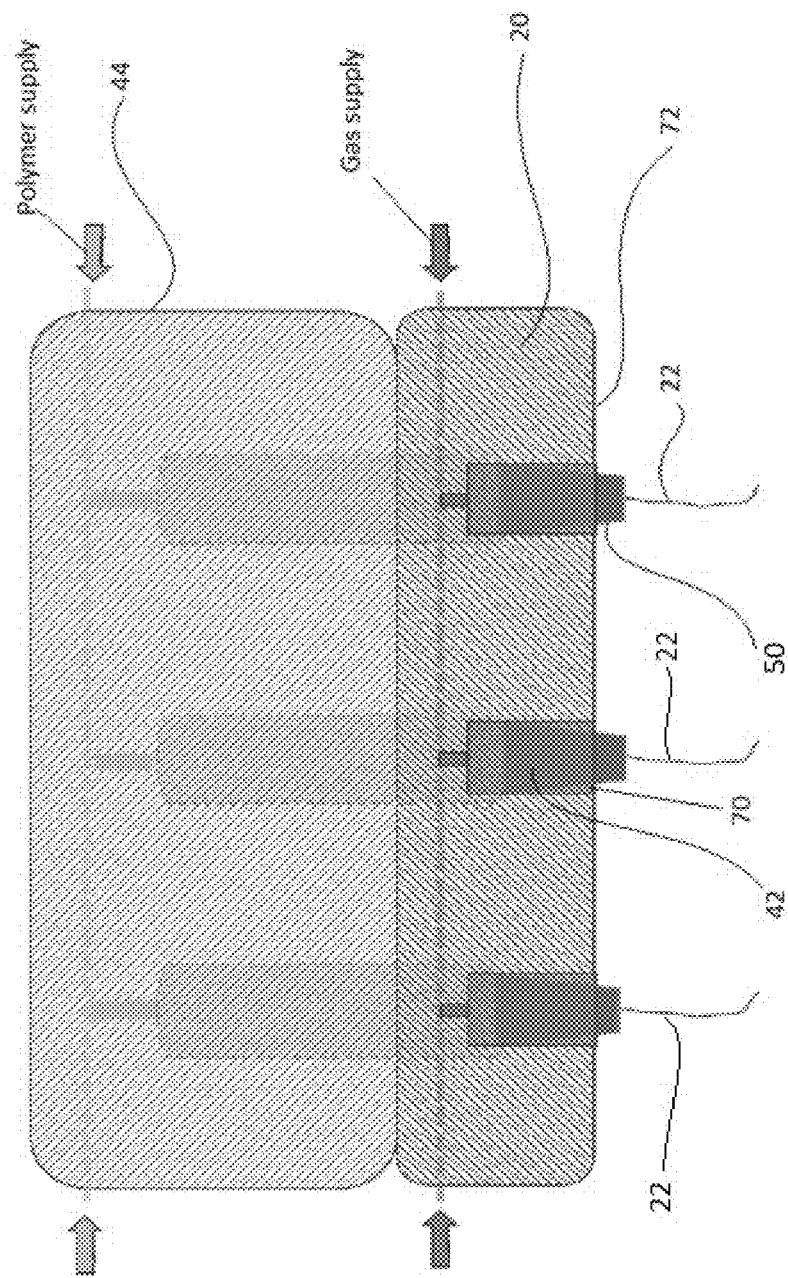
Figure 12B:
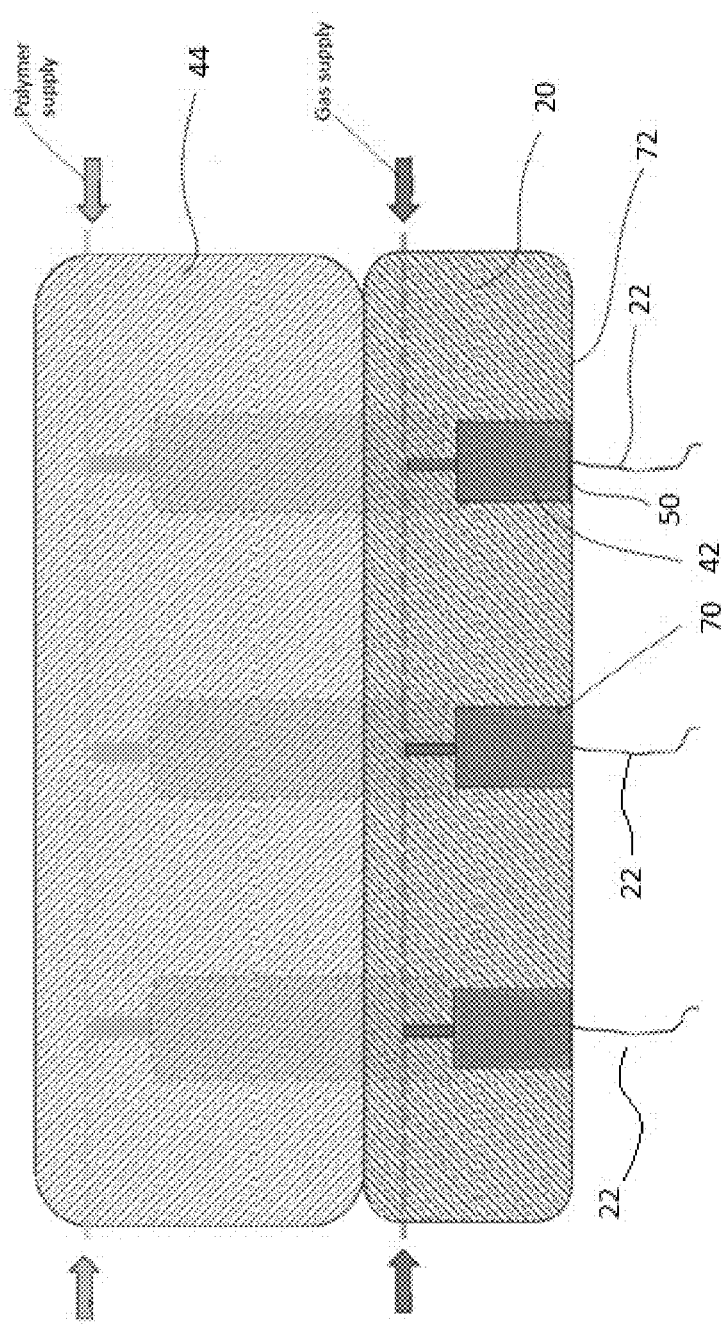
Figure 12C:
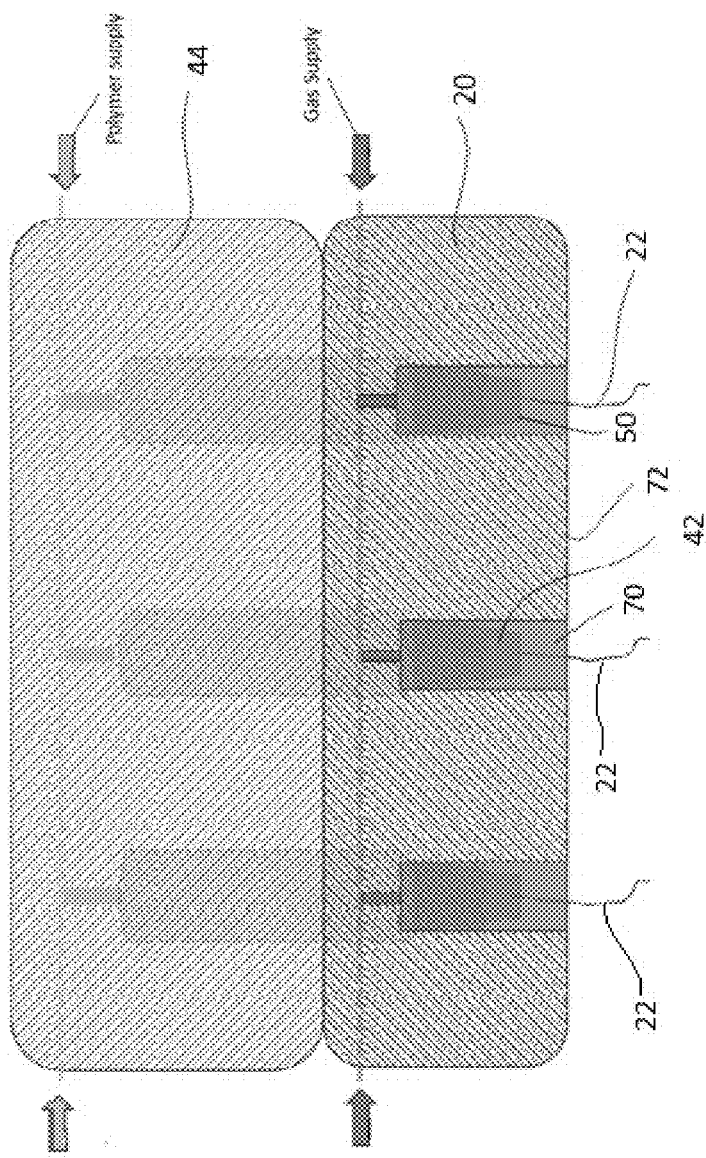
Figure 13:
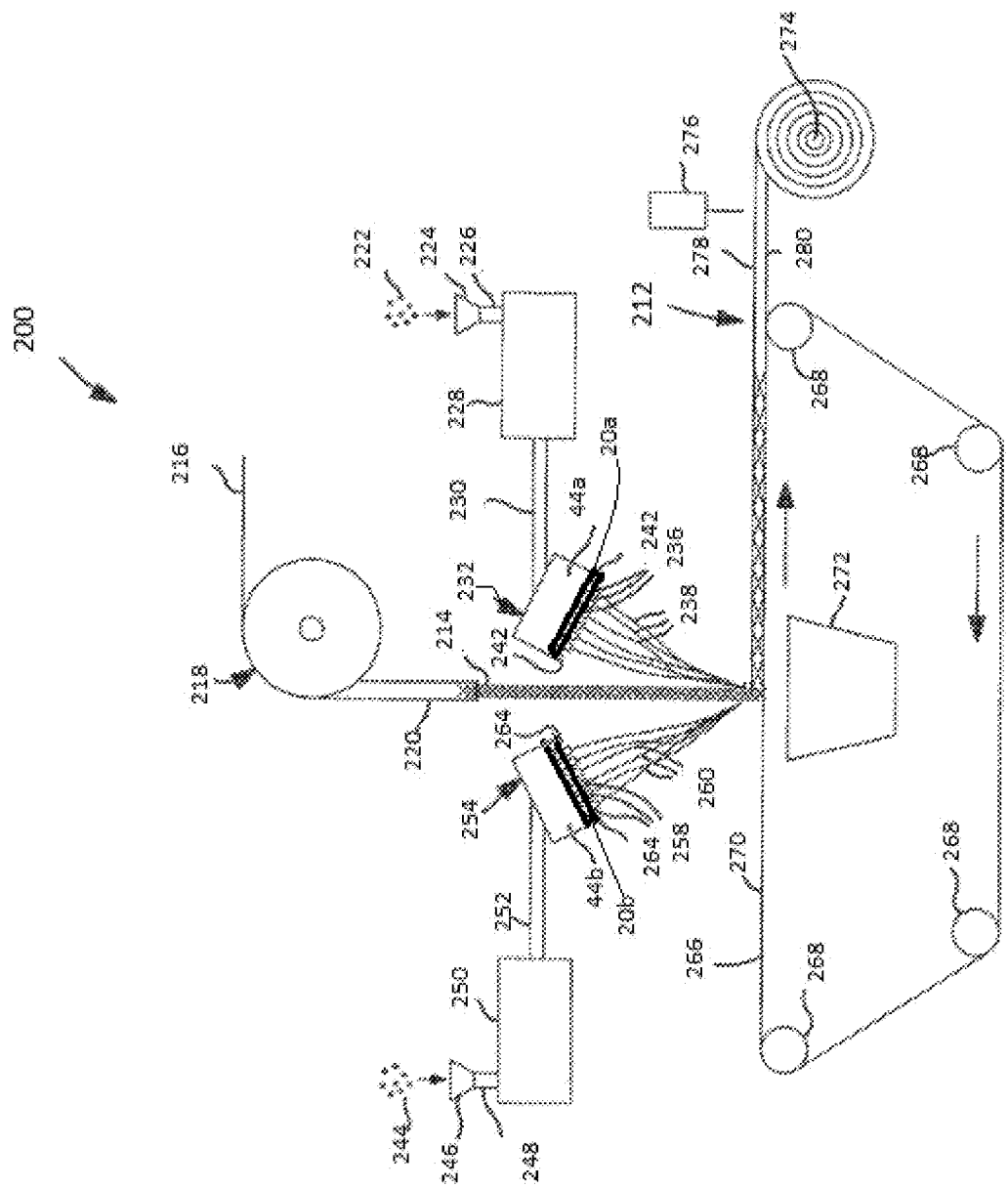
Figure 14:
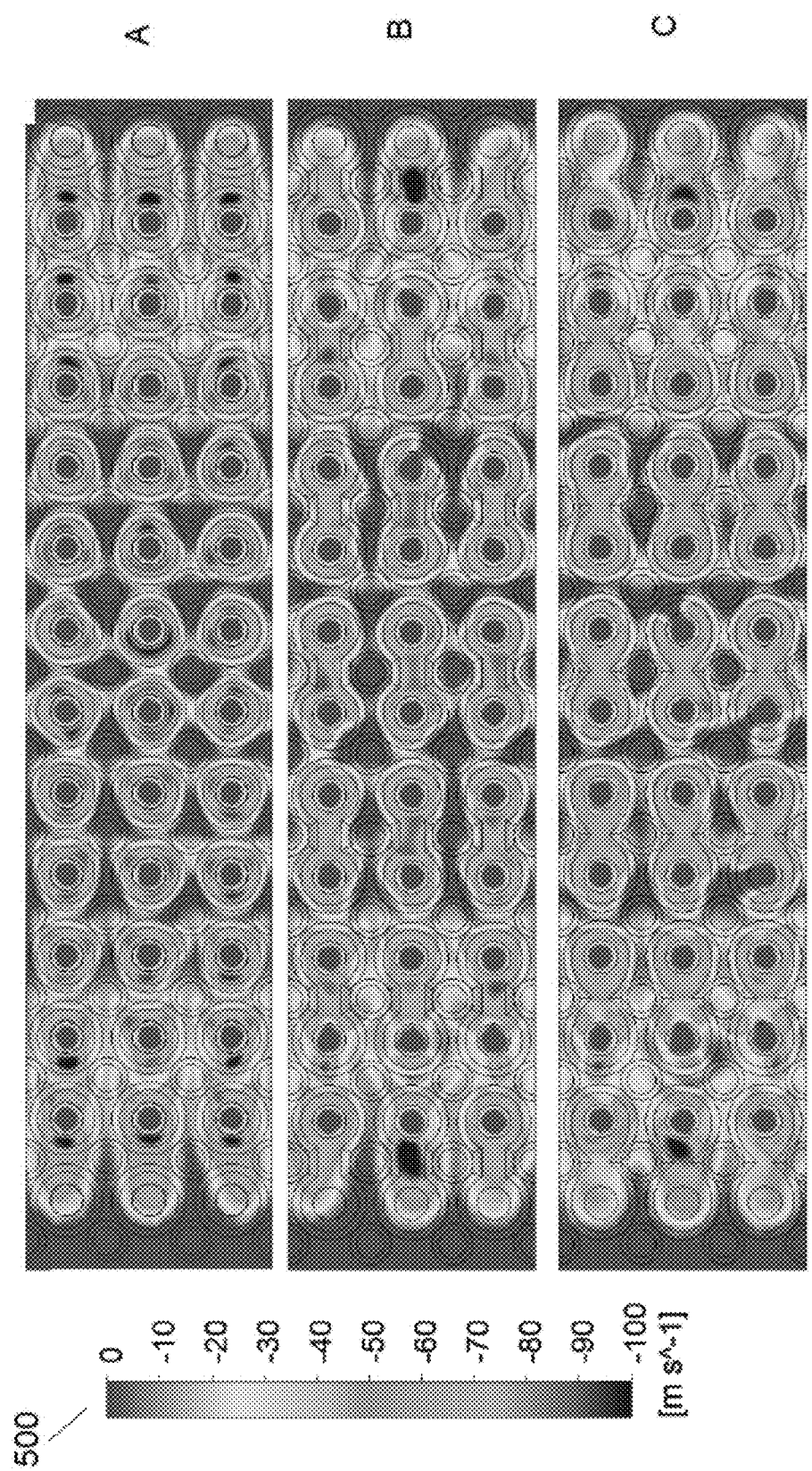

Having thus described the invention in general terms, reference will now be made to the accompanying drawings, which are not necessarily drawn to scale, and wherein:

FIG. 1 is a schematic illustration of a system and process in accordance with at least one embodiment of the present invention;

FIG. 2 is a schematic illustration of a system and process in accordance with at least one embodiment of the present invention;

FIG. 3 illustrates a lower surface of a spinneret having a plurality of filament nozzles arranged in columns and rows;

FIG. 4 is a partial cross-section view of a spinneret having a plurality of filament nozzles in accordance with at least one embodiment of the invention;

FIG. 5A is bottom view of a spinneret assembly having a plurality of filament nozzles arranged in columns and rows;

FIG. 5B is a bottom view of a gas distribution plate comprising a plurality of gas distribution slots;

FIG. 5C is a bottom view of an assembled spinneret assembly and gas distribution plate;

FIG. 5D is cross-section view of the assembled spinneret assembly and gas distribution plate taken along line 5D of FIG. 5C;

FIG. 6A is a bottom view of a gas distribution plate comprising a plurality of gas distribution slots;

FIG. 6B is a bottom view of an assembled spinneret assembly and gas distribution plate;

FIG. 6C is cross-section view of the assembled spinneret assembly and gas distribution plate taken along line 6C of FIG. 6B;

FIGS. 7A and 7B illustrate two embodiments of assembled spinneret assemblies in which the rows of filament nozzles and rows of gas distribution slots are arranged in an alternating pattern;

FIGS. 8A-8I illustrate various bottom views of an assembled spinneret assembly and gas distribution plate in which the gas distribution plate comprises a plurality of segmented slots of different shapes;

FIGS. 9A and 9B provide a bottom view of an assembled spinneret assembly and gas distribution plate in which the gas distribution plate comprises a plurality of segmented slots and a plurality of individual gas distribution outlets;

FIG. 10 is a cross-sectional view of an assembled spinneret assembly and gas distribution plate in accordance with at least one embodiment of the invention;

FIGS. 11A and 11B are cross-sectional views of an assembled spinneret assembly and gas distribution plate in accordance with at least one embodiment of the invention;

FIGS. 12A-12C are cross-sectional views of an assembled spinneret assembly and gas distribution plate in accordance with at least one embodiment of the invention;

FIG. 13 is a schematic illustration of a system for preparing a composite nonwoven fabric in accordance with at least one embodiment of the invention; and FIG. 14 depicts a virtual simulation of fluid flow through various configurations of gas distribution plates.

DETAILED DESCRIPTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used in the specification, and in the appended claims, the singular forms "a", "an", "the", include plural referents unless the context clearly dictates otherwise.

I. Definitions

For the purposes of the present application, the following terms shall have the following meanings:

The term "fiber" can refer to a fiber of finite length or a filament of infinite length.

The term "staple fiber" refers to a fibers of finite length. In general staple fibers used in preparing a carded fabric may have a length from about 15 to 65 millimeters (mm), and in particular, from about 20 to 50 mm, and more particularly, from about 25 to 40 mm.

The term "filament" refers to fibers of continuous or substantially continuous length.

As used herein, the term "monocomponent" refers to fibers formed from one polymer or formed from a single blend of polymers. Of course, this does not exclude fibers to which additives have been added for color, anti-static properties, lubrication, hydrophilicity, liquid repellency, etc.

As used herein, the term "multicomponent" refers to fibers formed from at least two polymers (e.g., bicomponent fibers) that are extruded from separate extruders. The at least two polymers can each independently be the same or different from each other, or be a blend of polymers. The polymers are arranged in substantially constantly positioned distinct zones across the cross-section of the fibers. The components may be arranged in any desired configuration, such as sheath-core, side-by-side, pie, island-in-the-sea, and so forth. Various methods for forming multicomponent fibers are described in U.S. Pat. No. 4,789,592 to Taniguchi et al. and U.S. Pat. No. 5,336,552 to Strack et al., U.S. Pat. No. 5,108,820 to Kaneko, et al., U.S. Pat. No. 4,795,668 to Kruege, et al., U.S. Pat. No. 5,382,400 to Pike, et al., U.S. Pat. No. 5,336,552 to Strack, et al., and U.S. Pat. No. 6,200,669 to Marmon, et al., which are incorporated herein in their entirety by reference. Multicomponent fibers having various irregular shapes may also be formed, such as described in U.S. Pat. No. 5,277,976 to Hogle, et al., U.S. Pat. No. 5,162,074 to Hills, U.S. Pat. No. 5,466,410 to Hills, U.S. Pat. No. 5,069,970 to Largman, et al., and U.S. Pat. No. 5,057,368 to Largman, et al., which are incorporated herein in their entirety by reference.

As used herein, the terms "nonwoven," "nonwoven web" and "nonwoven fabric" refer to a structure or a web of material which has been formed without use of weaving or knitting processes to produce a structure of individual fibers or threads which are intermeshed, but not in an identifiable, repeating manner. Nonwoven webs have been, in the past, formed by a variety of conventional processes such as, for example, meltblown processes, spunbond processes, and staple fiber carding processes.

As used herein, the term "carded fabric" refers to a nonwoven fabric comprising staple fibers that are predominantly aligned and oriented in the machine direction using a carding process. Processes and systems for preparing carded fabrics are disclosed, for example, in U.S. Pat. Nos. 3,145,425 and 5,494,736.

As used herein, the term "meltblown" refers to a process in which fibers are formed by extruding a molten thermoplastic material through a plurality of fine, usually circular, die capillaries into a high velocity gas (e.g. air) stream which attenuates the molten thermoplastic material and forms fibers, which can be to microfiber diameter. Thereafter, the meltblown fibers are carried by the gas stream and are deposited on a collecting surface to form a web of random meltblown fibers. Such a process is disclosed, for example, in U.S. Pat. No. 3,849,241 to Buntin et al. In some embodiments, the high velocity gas is heated.

As used herein, the term "machine direction" or "MD" refers to the direction of travel of the nonwoven web during manufacturing.

As used herein, the term "cross direction" or "CD" refers to a direction that is perpendicular to the machine direction and extends laterally across the width of the nonwoven web.

As used herein, the term "spunbond" refers to a process involving extruding a molten thermoplastic material as filaments from a plurality of fine, usually circular, capillaries of a spinneret, with the filaments then being attenuated and drawn mechanically or pneumatically. The filaments are deposited on a collecting surface to form a web of randomly arranged substantially continuous filaments which can thereafter be bonded together to form a coherent nonwoven fabric. The production of spunbond non-woven webs is illustrated in patents such as, for example, U.S. Pat. Nos. 3,338,992; 3,692,613, 3,802,817; 4,405,297 and 5,665,300. In general, these spunbond processes include extruding the filaments from a spinneret, quenching the filaments with a flow of air to hasten the solidification of the molten filaments, attenuating the filaments by applying a draw tension, either by pneumatically entraining the filaments in an air stream or mechanically by wrapping them around mechanical draw rolls, depositing the drawn filaments onto a foraminous collection surface to form a web, and bonding the web of loose filaments into a nonwoven fabric. The bonding can be any thermal or chemical bonding treatment, with thermal point bonding being typical.

As used herein, the terms "hydro-bonding," "hydroentangled," and "hydraulically entangled" involves subjecting a material such as one or more webs of fibers to be bonded below a plurality of nozzles/jets that provide one or more high pressure jets of water which impinge on the surface of the material. The jets of high pressure water penetrate into the web of fibers causing the fibers of adjacent layers to be mechanically entangled with each other, and thereby bond the layers of the web to each other.

As used herein, the term "air through thermal bonding" involves passing a material such as one or more webs of fibers to be bonded through a stream of heated gas, such as air, in which the temperature of the heated gas is above the softening or melting temperature of at least one polymer component of the material being bonded. Air through thermal bonding may also involve passing a material through a heated oven.

As used herein, the term "thermal point bonding" involves passing a material such as one or more webs of fibers to be bonded between a heated calender roll and an anvil roll. The calender roll is typically patterned so that the fabric is bonded in discrete point bond sites rather than being bonded across its entire surface.

As used herein, the term "polymer" generally includes, but is not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material, including isotactic, syndiotactic and random symmetries.

The term "composite", as used herein, refers to a sheet material, such as a nonwoven web, comprising a mixture of two different fibers. The mixture of fibers may be homogeneous or heterogeneous throughout the composite structure. In addition, the term "composite" may be a structure comprising two or more layers, such as a fiber layer or a plurality of fiber layers bonded together. The two layers of a composite structure may be joined together such that a substantial portion of their common X-Y plane interface, according to certain embodiments of the invention.

The terms "about" and "substantially" as used herein means a deviation (plus/minus) of less than 10%, and in particular, less than 5%, less than 4%, less than 3%, less than 2%, and less than 1% of the recited value.

In certain aspects, embodiments of the invention are directed to a system and process for preparing a nonwoven fabric comprising a plurality of thermoplastic fibers that are bonded together to form a coherent web.

I. Representative System and Process for Preparing Nonwoven Fabrics

With reference to FIG. 1, a system and process for preparing a fibrous nonwoven fabric is shown and designated by reference character 10. As shown, the system includes a first polymer source (i.e., hopper 12) that is in fluid communication with a spin beam 16 via the extruder 14. In certain embodiments, the spin beam 16 includes a die block 18 for delivering molten polymer streams to a plurality of filament nozzles (not shown) and a gas distribution plate 20 disposed downstream of the die block 18.

In some embodiments, the die block 18 may include a plurality of meters and pumps that deliver one or more polymer streams to the plurality of filament nozzles. In some embodiments, the die block 18 may include one or more heating elements to maintain the molten polymer streams at a desired temperature.

In the die block 18, at least one molten polymer stream is distributed to plurality of filament nozzles (e.g., spinnerets) from which the molten polymer streams are extruded as a curtain of continuous or semi-continuous filaments 22.

Die block 18 may include a cavity (not shown) in which the molten polymer is introduced prior to being extruded through the plurality of filament nozzles. The die block may also include one or more polymer distribution plates and filters (not shown).

Gas distribution plate 20 is disposed downstream of the die block 18. Gas distribution plate 20 is configured and arranged to distribute a plurality of streams of gas that draw and attenuate the filaments 22 as the filaments are extruded from the plurality of filament nozzles. As used herein, the term "gas" refers to a state of matter distinguished from the solid and liquid states by relatively low density and the spontaneous tendency to be uniformly distributed throughout any container. In one embodiment, the gas comprises a mixture of predominately nitrogen (approximately 78%), oxygen (approximately 21%) with lesser amounts of other gas. The gas streams are provided by a gas source (not shown) that is in fluid communication with the gas distribution plate 20. In a preferred embodiment, the gas distribution plate is disposed immediately downstream of lower surface of die block 18.

The drawn and attenuated filaments 22 are then deposited onto a collection surface 24 to form a nonwoven web 26. In certain embodiments, the extruded filaments may be introduced into the quenching station (not shown) in which the filaments are exposed to quenching air and/or water streams directed at the filaments, and may further be drawn into a drawing station (not shown), which further draws and attenuates the filaments. In some embodiments, the drawn filaments may be introduced into a diffuser (not shown) prior to being deposited onto the collection surface.

In certain embodiments, the nonwoven web 26 may be passed through a bonding station 30 in which the filaments are bonded to form a coherent web. A wide variety of bonding methods may be used in accordance with the invention including thermal bonding (e.g., through air bonding, calender bonding, ultrasonic bonding, and the like), mechanical bonding (e.g., hydroentanglement or needle punching) and chemical bonding (e.g., use of an adhesive resin). In one embodiment, the bonding station comprises a thermal bonding unit comprising a pair of opposing calender rolls.

In some embodiments, the nonwoven web 26 may be passed through an embossing station to impart a desired pattern to the surface of the web. In one such example, the embossing station may comprises a thermal embossing unit comprising a pair of opposing calender rolls. Ultrasonic bonding may also be used to emboss the surface of the nonwoven web.

In certain embodiments, the bonding unit comprises a chamber in which the nonwoven fabric is exposed to a stream of heated gas, such as air, and in which the temperature of the heated gas is above the softening or melting temperature of at least one polymer component of the nonwoven fabric.

In some embodiments, the bonding unit may comprise a hot air knife which is configured to subject the nonwoven fabric to a stream of heated air that thermally bonds adjacent fibers to each other.

In further embodiments, the bonding unit may comprise one or more hydraulic entanglement units which are configured to subject the nonwoven fabric to streams of high pressure water that causes the fibers to intertwine and mechanically bond together.

In some embodiments, the system may also include a pair of cooperating rolls (not shown) (also referred to herein as a "press roll") positioned downstream from the outlet of the spin beam. In this regard, the press roll may be configured to stabilize the web of filaments by compressing web prior to delivering the web of fibers from the outlet of the spin beam towards the bonding unit. In some embodiments, for example, the press roll may include a ceramic coating deposited on a surface thereof. The press roll may be heated or cooled. In certain embodiments, for instance, one roll of the pair of cooperating rolls may be positioned above the collection surface 24, and a second roll of the pair of cooperating rolls may be positioned below the collection surface 24.

In some embodiments and as shown in FIG. 1, the system may comprise a vacuum source 28 disposed below the collection surface 24 for pulling the plurality of continuous/semi-continuous filaments from the outlet of the spin beam onto the collection surface before delivery to the optional bonding unit.

Finally, the nonwoven fabric moves to a winder 32 where the fabric is wound onto rolls.

In the embodiment illustrated in FIG. 1, a single extruder and hopper are shown for delivering a single polymer stream from the extruder to the spin beam 16. In other embodiments, the system may include two or more hoppers and extruders in communication with the spin beam. In this regard, FIG. 2 illustrates a system 10*a* comprising second polymer source (i.e., hopper 12*a*) and second extruder 14*a* that are in fluid communication with spin beam 16 and are configured and arranged to deliver a second stream of molten polymer to the spin beam 16.

Although FIG. 2 only shows two polymer sources (e.g., two hoppers/extruders) for providing two molten polymeric streams to the spin beam, it should be recognized that the system may include additional polymer sources (additional hoppers and extruders) for supplying additional molten polymeric streams to the spin beam. In one embodiment, the system may include three polymer sources for providing three molten polymeric streams to the spin beam.

In some embodiments, the system may include additional devices for further modifying or treating the nonwoven fabric. For example, the system may include a kiss roller or similar device for applying topical treatments, such as a surfactant, to a surface of the nonwoven fabric. In some embodiments, the system may also include one or more devices for incrementally stretching the fabric. An example of such a device is a ring roller, which comprises a plurality of intermeshing rings that stretch select regions of the fabric.

Additionally, the filaments nozzles may include a variety of different shapes (e.g., round, square, oval, keyhole shaped, multi-lobal, such as trilobal, etc.), resulting in varying types of resultant fiber cross-sectional geometries.

In certain embodiments, the spin beam may be configured and arranged to produce monocomponent filaments. Monocomponent filaments may comprise a single type of polymer or a blend of two or more polymers. In certain other embodiments, the spin beam may be configured to produce multicomponent filaments in which the cross sections of the filaments comprise two or more polymer components. In certain embodiments, the filaments have a bicomponent configuration comprising a first polymer component and a second polymer component. In some embodiments, the first polymer component may comprise a polymer or blend of polymers that is different from the second polymer component. In other embodiments, the first polymer component and the second polymer component may comprise the same polymer or the same blend of polymers. Examples of multicomponent fibers may include fibers having a side-by-side configuration, sheath/core configuration, eccentric sheath/core configuration, D-centric sheath/core configuration, tricomponent configuration, or a bico-segmented pie configuration, and the like.

Referring to FIG. 3, a lower surface 40 of the die block 18 includes a spinneret assembly 44 comprising a plurality of filament nozzles 42 that are arranged in arrays extending in the cross-direction of the spin beam. For example, the die block may include two or more rows of filament nozzles arranged in a substantially horizontal, rectangular array, typically from 30 to 200 filament nozzles per cm of length of the die block. As used herein, the term "spinneret" refers to the lower most portion of the spin pack that delivers the molten polymer to and through filament nozzles for extrusion to form continuous or semi-continuous filaments. The plurality of filament nozzles can be implemented with holes drilled or etched through a plate or any other structure capable of issuing the required fiber streams.

In certain embodiments, the spinneret assembly 44 comprises a plate that is attached to a downstream portion of the die block 18 to which the plurality of filament nozzles 42 are formed or attached. In other embodiments, the spinneret assembly is an integral part of the die block 18.

In some embodiments, the plurality of filament nozzles 42 are releasably attached to the spinneret assembly 44. Attachment of the plurality of filament nozzles may be achieved with corresponding male/female threads disposed on the filament nozzles and an associated opening on the spinneret assembly, clamps, locking bolts, nuts and screws (e.g., hex bolts, socket screws, machine screws, and set screws), and the like.

In certain embodiments, the filament nozzle may comprise a projecting part with an opening, as at the end of a hose, for regulating and directing the flow of a fluid or molten material. In some embodiments, each of the filament nozzles 42 comprises a projecting part that is secured to the spinneret assembly 44. Each of the filament nozzles 42 is spaced apart from an adjacent nozzle 42. In the spinneret assembly 44, the number of filament nozzles 42 can vary. A spinneret assembly 44 can contain from as few as ten filament nozzles 42 to several thousand filament nozzles 42. For a commercial size line, the number of filament nozzles 42 in the spinneret assembly 44 can range from between about 1,000 to about 10,000. Desirably, the spinneret assembly 44 will have at least about 1,500 filament nozzles. More desirably, the spinneret assembly 44 will have at least about 2,000 filament nozzles. Even more desirably, the spinneret assembly 44 will have at least about 2,500 filament nozzles. Most desirably, the spinneret assembly 44 will have 3,000 or more nozzles.

The size of the filament nozzles 42 can vary. The size of the filament nozzles 42 can range from between about 50 microns to about 1,000 microns. More desirably, the size of the filament nozzles 42 can range from between about 150 microns to about 700 microns. More desirably, the size of the filament nozzles 42 can range from between about 20 microns to about 600 microns. Filament nozzles of various size can be used, but generally all of the nozzles have the same size.

The filament nozzles 42 can be formed from a metal, such as steel, stainless, a metal alloy, a ferrous metal, etc. In certain embodiments, each of the filament nozzles 42 is formed from stainless steel.

With reference to FIG. 4, a cross-sectional side view of the spinneret assembly 44 is shown. The spinneret assembly 44 includes a plurality of spaced apart filament nozzles 42. The spinneret assembly includes an upper surface 48 and a lower surface 40. In some embodiments, the filament nozzles 42 may generally have an elongated tubular body 46 having a hollow tube structure. By "tube" it is meant a hollow cylinder, especially one that conveys fluid or functions as a passage. Each of the hollow, cylindrical tubes includes a distal end 50 and a proximal end 52. In the illustrated embodiment, the proximal end 52 of the tubular bodies 46 are in fluid communication with a polymer source via one or more polymer supply channels 56. In some embodiments, the proximal end of the tubular bodies 46 are open and in fluid communication with a cavity in the die block from which molten polymer is supplied to each of the tubes.

The distal end of the tubular body 46 includes an opening 54 from which streams of molten polymer are extruded to form continuous or semi-continuous filaments 22. In certain embodiments, the distal ends 50 of the filament nozzles 42 may have a generally conical shape as shown in FIG. 4. In other embodiments, the distal ends 50 of the filament nozzles may have a generally planar shape. In other words, they do not taper towards opening 54.

In the embodiment illustrated in FIG. 4, the filaments nozzles are depicted as extending below the lower surface 40 of the spinneret assembly 44. In other embodiments, the distal ends 50 of the filament nozzles may be coterminous or substantially planar with lower surface 40 of the spinneret assembly 44.

In a preferred embodiment, the inside cross-section of each tubular body 46 is circular in shape and constant throughout its length. The length of each of the filament nozzles can vary. Typically, the length of a filament nozzle 42 ranges from between about 0.5 to about 6 inches. Although a circular cross section is preferred, it should be recognized that the filaments nozzles may include a variety of different cross-sectional shapes (e.g., square, oval, torus, keyhole shaped, multi-lobal, such as trilobal, etc.), resulting in varying types of resultant fiber cross-sectional geometries.

Each of the filament nozzles 42, in the form of a hollow, cylindrical tubular body 46, has an inside diameter and an outside diameter. The inside diameter can range from between about 0.125 millimeters (mm) to about 1.25 mm. The outside diameter of each filament nozzle 42 should be at least about 0.5 mm, and in particular, the outside diameter of each nozzle 42 can range from between about 0.5 mm to about 2.5 mm.

Referring back to FIG. 3, the plurality of filament nozzles 42 are typically grouped into an array of a plurality of rows (designated by reference character "R") that extend in the cross direction of the spin beam, and a plurality of columns (designated by reference character "C") that extend in the machine direction of the spin beam. The number of rows can vary as well as the number of columns. Typically, the number of rows will be from about 2 to 60, and in particular, from about 3 to 30, and more particularly, from about 5 to 20. In certain embodiments, the number of rows of filament nozzles will range from about 5 to 15.

Typically, the number of columns "C" will range from about 50 to about 500. In particular, the number of columns may range from about 60 to about 450, and more particularly, the number of columns may range from about 100 to about 300. In certain embodiments, the number of columns may range from about 150 to about 250. In some embodiments, the number of columns will be greater than 200.

In certain embodiments, gas distribution plate 20 includes a plurality of gas distribution slots that are associated with one or more rows or columns of the plurality of filament nozzles of the spinneret assembly. As discussed in greater detail below, the gas distribution plate 20 includes an upper surface that is disposed downstream of the lower surface of the spinneret assembly. The gas distribution slots are configured and arranged to provide a stream of gas that draws and attenuates the filaments as they are extruded from the plurality of filament nozzles.

In this regard, FIGS. 5A-5D illustrate an embodiment in which the die block of the spin beam comprises a gas distribution plate 20 having a plurality of gas distribution slots that extend in the machine direction of the spin beam. The spinneret assembly comprises a plurality of filament nozzles 42 arranged in columns in which each column is associated with a corresponding gas distribution slot 70 of the gas distribution plate 20.

FIG. 5A illustrates the lower surface 40 of the spinneret assembly 44 having a plurality of filament nozzles 42 arranged in rows and columns. As shown, the plurality of nozzles are arranged in columns ("C") that extend in the machine direction ("MD") of the spin beam. FIG. 5B illustrates the lower surface 72 of the gas distribution plate 20 having a plurality of spaced apart gas distribution slots 70 that extend longitudinally across the gas distribution plate 20 in the machine direction of the spin beam (see FIG. 1, reference character 16).

With reference to FIG. 5C, the spinneret assembly (see FIG. 4, reference character 44) and the gas distribution plate 20 are depicted in an assembled state in which the lower surface 72 of the gas distribution plate 20 is shown. As can be seen, each column C of the plurality of filament nozzles is associated with a corresponding gas distribution slot 70 of the gas distribution plate. As noted above, the columns of filament nozzles and corresponding gas distribution slots extend in the machine direction of the spin beam. In this embodiment, the plurality of filament nozzles, which are arranged in a column extending in the machine direction of the spin beam, are disposed within a corresponding gas distribution slot of the gas distribution plate. In some embodiments, the plurality of filament nozzles may be disposed at least partially within the corresponding gas distribution slot.

In certain other embodiments, the plurality of filament nozzles extend completely through the corresponding gas distribution slot such that the distal ends of the filament nozzles are disposed below the lower surface of the gas distribution plate.

In one embodiment, the gas distribution plate 20 and spinneret assembly 44 are joined to the spin beam via one or more fasteners 76, such as a bolt. In this regard, it is noted that FIGS. 5A and 5B show that each of the gas distribution plate 20 and spinneret assembly 44 include corresponding bores 60 through fasteners may be inserted for joining the gas distribution plate 20 and spinneret assembly 44 to the spin beam.

With reference to FIG. 5D, a cross-sectional view of the spinneret assembly 44 and the gas distribution plate 20 in an assembled state taken along line 5D of FIG. 5C is illustrated. As shown, the gas distribution plate 20 is depicted overlying the spinneret assembly 44; however, it should be recognized that in the actual assembly the orientation of the plates would be flipped such that the gas distribution plate would underly the spinneret assembly. In other words, the gas distribution plate would be disposed downstream of the spinneret assembly such that the plurality of filament nozzles extend downwardly from the lower surface of the spinneret assembly.

In this embodiment, each column comprising a plurality of filament nozzles 42 extend outwardly from the spinneret assembly, through a corresponding gas distribution slot 70 and extend downwardly beneath the lower surface 72 of the gas distribution plate 20. Molten polymer may be supplied to each of the filament nozzles via one or more polymer supply channels 80. In some embodiments, each individual filament nozzle 42 may be in fluid communication with a polymer supply channel 80 via an inlet channel 80a.

A stream of gas is provided to each of the gas distribution slots via one or more gas inlet channels 78a that are in fluid communication with one or more gas supply manifolds 78. As noted previously, gas supply manifolds are in fluid communication with a gas source, such as pressurized air.

In other embodiments, the gas distribution slots 70 of the gas distribution plate may extend in the cross-direction of the spin beam. In this regard, FIGS. 6A-6C illustrate an embodiment of the invention in which the gas distribution slots extend laterally in the cross-direction ("CD") of the spin beam.

FIG. 6A illustrates the lower surface 72 of the gas distribution plate 20. In this embodiment, the gas distribution plate 20 comprises a plurality of spaced apart gas distribution slots 70 that extend in the cross-direction of the spin beam.

FIG. 6B illustrates the spinneret assembly 44 (not visible) and the gas distribution plate 20 in an assembled state in which the lower surface 72 of the gas distribution plate 20 is shown. As can be seen, the plurality of filament nozzles 42 are arranged in rows ("R") that extend in the cross direction of the spin beam. Each row R of the plurality of filament nozzles is associated with a corresponding gas distribution slot 70 of the gas distribution plate. As noted above, the rows of filament nozzles and corresponding gas distribution slots extend in the cross-direction of the spin beam.

FIG. 6C provides a cross-sectional view of the spinneret assembly 44 and the gas distribution plate 20 taken along line 6C of FIG. 6B. As shown, the gas distribution plate 20 is depicted overlying the spinneret assembly 44; however, it should be recognized that in the actual assembly the orientation of the plates would be flipped such that the gas distribution plate would underly the spinneret assembly. In other words, the gas distribution plate is disposed downstream of the spinneret assembly such that the plurality of filament nozzles extend downwardly from the lower surface of the spinneret assembly.

In this embodiment, each row R comprising a plurality of filament nozzles 42 extend outwardly from the spinneret assembly, through a corresponding gas distribution slot 70 and extend downwardly beneath the lower surface 72 of the gas distribution plate 20. Molten polymer may be supplied to each of the filament nozzles via one or more polymer supply channels 80. In some embodiments, each individual filament nozzle 42 may be in fluid communication with polymer supply channels 80 via an inlet channel (see FIG. 5D, reference character 80a).

A stream of gas is provided to each of the gas distribution slots via one or more gas inlet channels (see FIG. 5D, reference character 78a) that are in fluid communication with one or more gas supply manifolds 78. As noted previously, gas supply manifolds are in fluid communication with a gas source, such as pressurized air.

With reference to FIG. 7A, an embodiment of the invention is illustrated in which the assembled spinneret assembly and gas distribution plate comprises a pattern of alternating gas distribution slots 70 and rows/columns 90 comprising a plurality of filament nozzles 42. In this embodiment, the rows or columns comprising the plurality of filament nozzles are not disposed within a corresponding gas distribution slot. Rather, the gas distribution plate 20 includes an alternating pattern of gas distribution slots 70 and rows of individual apertures 92 that are each configured and arranged to receive a corresponding filament nozzle 42 from the spinneret assembly. In an assembled state, the individual filament nozzles of each row extend at least partially into the corresponding aperture 92 of the gas distribution plate 20. As in the previous embodiments, the filament nozzles may extend partially or completely through the thickness of the gas distribution plate.

As shown in FIG. 7A, the gas distribution plate 20 includes two side edges 94a, 94b disposed on opposite sides of the gas distribution plate. Preferably, the outer edges of the alternating pattern of rows/columns of filament nozzles and the gas distribution slots are each terminated with a gas distribution slot so that each row/column of filament nozzles are disposed between a pair of gas distribution slots. In other words, each row/column of filament nozzles are preferably sandwiched between a pair of gas distribution slots. In this regard, a first terminal gas distribution slot 70a is disposed towards side edge 94a and a second terminal gas distribution slot 70b is disposed towards side edge 94b.

The spinneret assembly and gas distribution plate 20 may be attached to the spin beam with a plurality of fasteners 76.

FIG. 7B illustrates an embodiment of the invention that is similar to the embodiment described in FIG. 7A. In this illustrated embodiment, the gas distribution plate 20 further includes two additional gas distribution slots 70c, 70d that are disposed along opposite side edges 94c, 94d. In certain embodiments, gas distribution slots 70c, 70d that are configured and arranged so that they are parallel or substantially parallel to the pattern of alternating gas distribution slots 70 and rows/columns 90 comprising the plurality of filament nozzles 42.

Advantageously, gas distribution slots 70a, 70b, 70c, and 70d, collectively enclose the plurality of rows/columns of filament nozzles so that the extruded filaments are shrouded by an envelope of gas as the filaments are extruded from the plurality of filament nozzles.

Figure 8A:
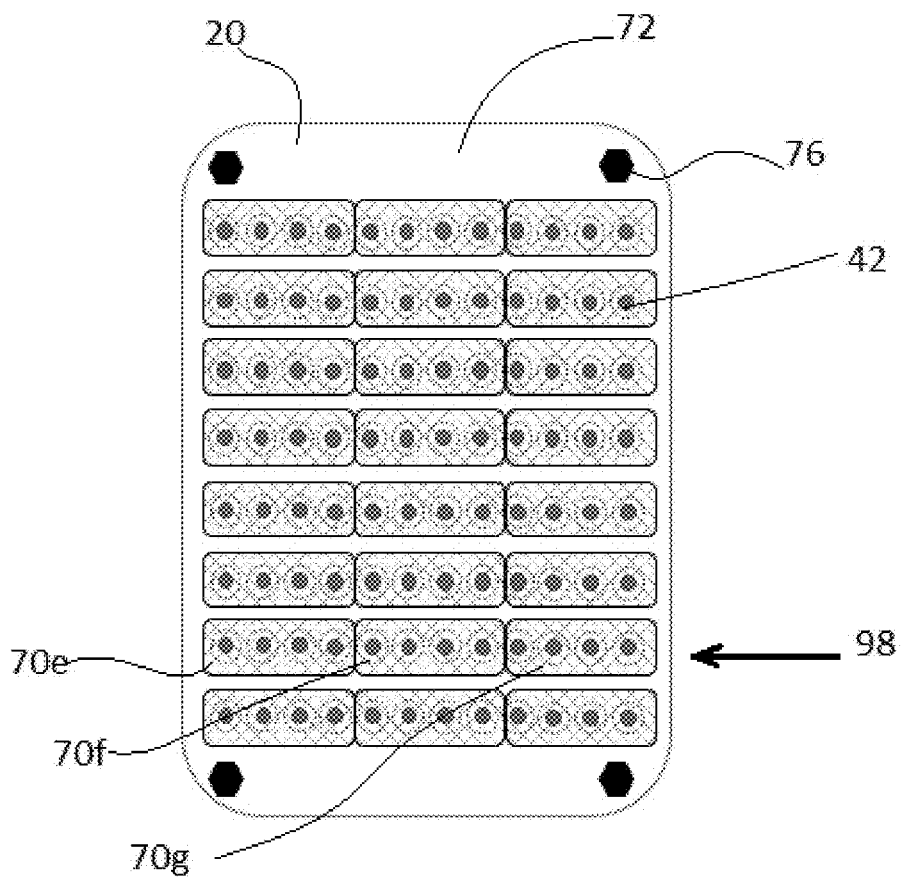

With reference to FIG. 8A, an embodiment of the invention is shown in which the gas distribution slots are segmented such that the gas distribution slot does not extend over the entire length of the row/column of filament nozzles. In this regard, FIG. 8A depicts an embodiment in which each row 98 of filament nozzles 42 is associated with a plurality of segmented gas distribution slots within a single row. In particular, gas distribution plate 20 includes a series of individual gas distribution slots 70e, 70f, 70g that collectively correspond to the filament nozzles 42 in a single row 98 of filament nozzles on the spinneret assembly. In the illustrated embodiment, each segmented gas distribution slot is shown as having four corresponding filament nozzles. However, it should be recognized that the number of filament nozzles associated with a corresponding gas distribution slot may be varied depending on the intended application and desired properties of the resulting nonwoven web.

In certain embodiments, the number of filament nozzles associated with a corresponding segmented gas distribution slot may range from 2 to 500, and in particular, 2 to 100, and more particularly, 2 to 50. In some embodiments, the number of filament nozzles associated with a corresponding segmented gas distribution slot may be from 4 to 20, such as 4 to 10.

In some embodiments, the plurality of segmented gas distributions slots may extend in the machine direction of the gas distribution plate. In certain embodiments, the plurality of segmented gas distributions slots may extend in the cross direction of the gas distribution plate.

Figure 8B:
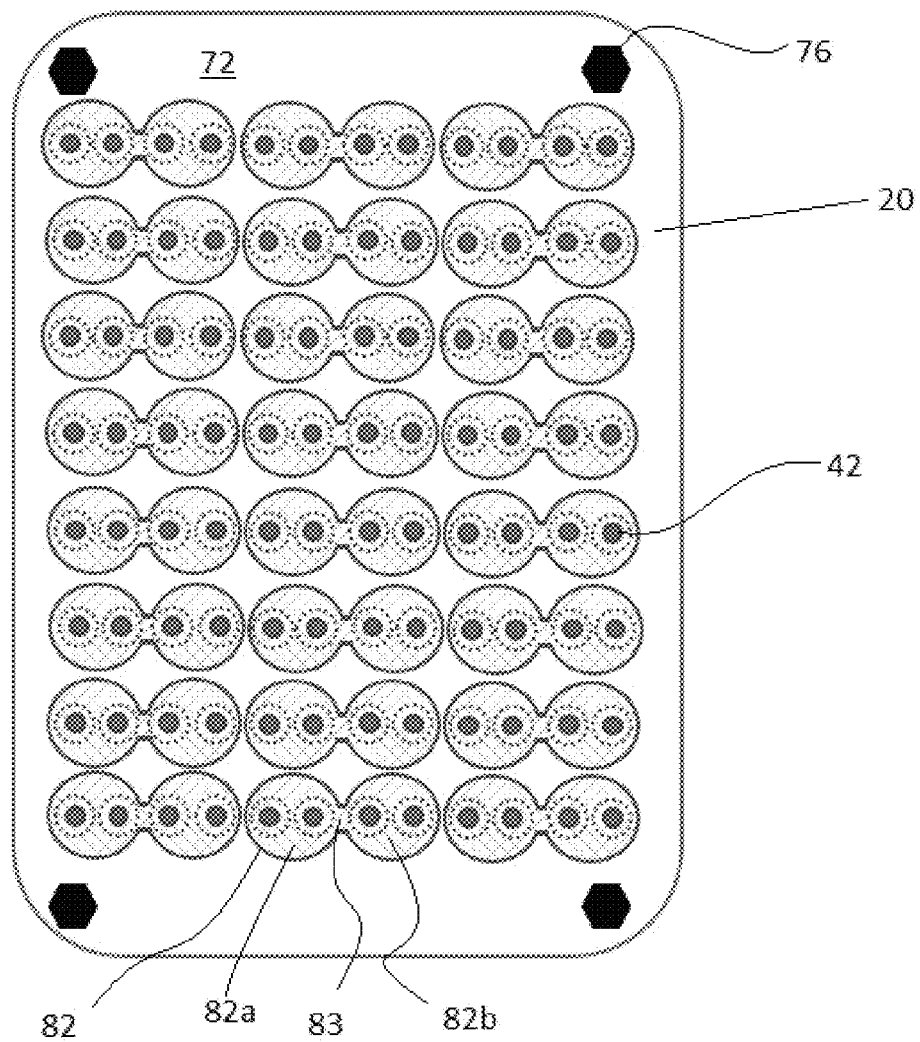
Figure 8C:
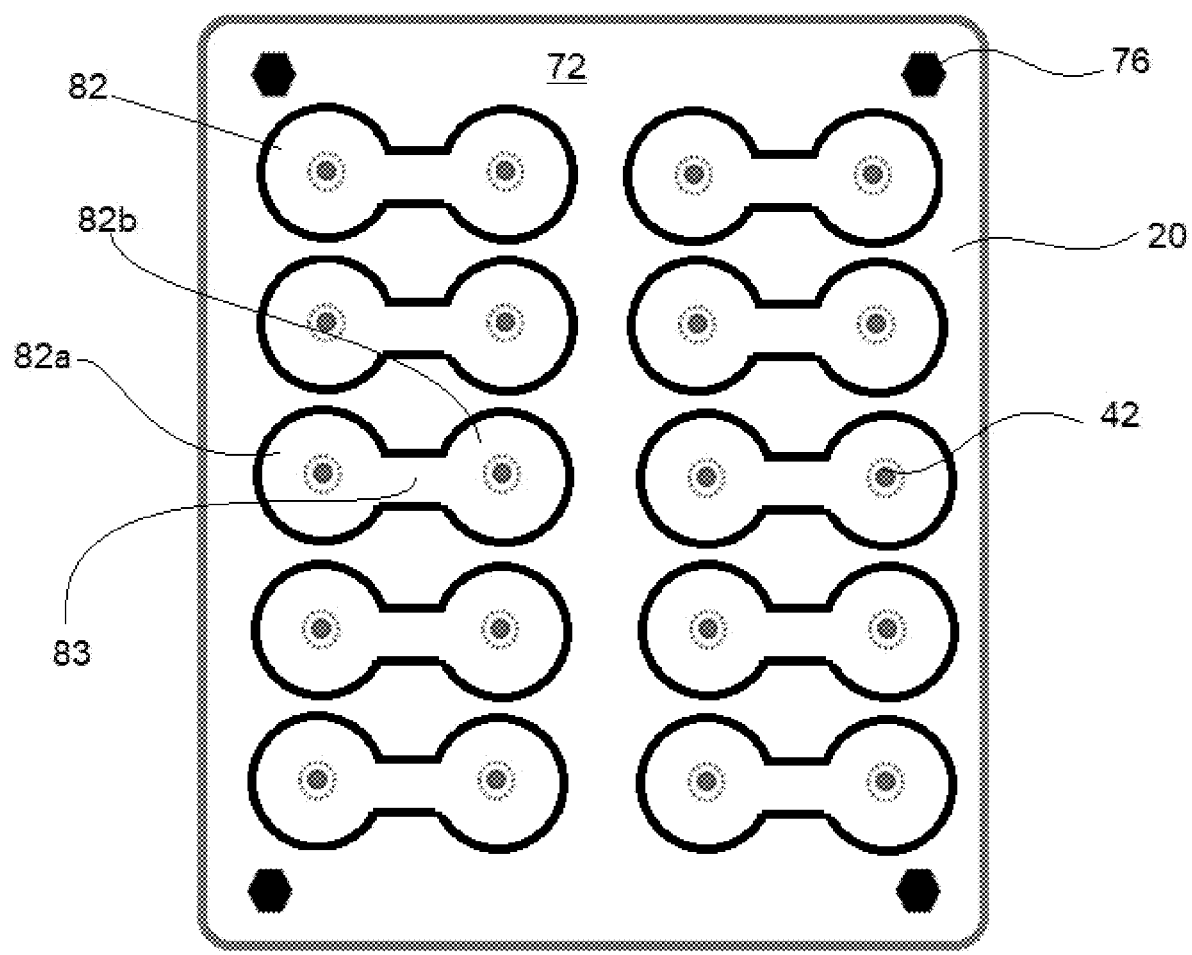

FIGS. 8B and 8C illustrate embodiments of the invention in which the which the gas distribution plate 20 includes a plurality of segmented gas distribution slots 82 having a generally dumb-bell shape comprising a pair of interconnected circular shaped gas chambers. As shown, a first circular chamber 82a is in fluid communication with a second circular chamber 82b via connecting fluid channel 83. In certain embodiments, the fluid connecting channel 83 has a width that is less than the diameters of the associated chambers 82a, 82b.

In certain embodiments, fluid connecting channel 83 helps to facilitate the distribution of gas between adjacent chambers so that a homogeneous flow of gas is maintained through the outlets of the gas distribution slots. In addition to facilitating the distribution of gas between adjacent chambers, the fluid connecting channel 83 helps to reduce or prevent adjacent filaments, which are in a molten or semi-molten state, from colliding during the polymer drawing phase thereby maintaining physical isolation and reducing filament roping.

Generally, the channel 83 has a width that is about 5 to 50 percent of the diameter of the associated circular chamber, with a width of about 10 to 30 percent being somewhat more preferred. The length (i.e., distance between the first and second chambers) of the fluid connecting channel 83 may vary depending on the desired properties of the nonwoven fabric. In certain embodiments, the length of the fluid connecting channel 83 may be from about 5 to 90 percent of the diameter of the associated chamber, with a width of about 10 to 30 percent being somewhat more preferred.

As shown in FIG. 8B, chambers 82a, 82b of gas distribution slot 82 collectively define an opening through which a stream of pressurized gas exits the die block of the spin beam. Each chamber includes at least one associated filament nozzle that is positioned within the chamber. As a stream of pressurized gas passes through the chamber, a filament extruded from the filament nozzle is within the field of influence of the pressurized gas. In the illustrated embodiment, each of the chambers 82a, 82b include two associated filament nozzles 42 so that the segmented gas distribution slot 82 includes four associated filament nozzles. It should be recognized that each chamber may include from about 1 to 20, and in particular, from 2 to 10, and more particularly, from 2 to 4 associated filament nozzles.

In the embodiment of FIG. 8B, only two adjacent chambers in the same row are depicted as being interconnected; however, it should be recognized that multiple adjacent chambers in both the machine direction and cross direction of the gas distribution plate may be interconnected. In some embodiments, all of the chambers in a row may be interconnected, and hence, in fluid communication, via a plurality of the fluid connecting channels 83. In some embodiments, all of the chambers in a column may be interconnected, and hence, in fluid communication, via a plurality of the fluid connecting channels 83. In certain embodiments, all of the chambers within the gas distribution chamber may be interconnected to each other.

Referring to FIG. 8C, chambers 82a, 82b of gas distribution slot 83 collectively define an opening through which a stream of pressurized gas exits the die block of the spin beam. In some embodiments, the stream of pressurized gas may be heated. Each chamber includes at least one associated filament nozzle 42 that is positioned within the associated chamber. In the illustrated embodiment, each of the chambers 82a, 82b includes one associated filament nozzles 42 so that the segmented gas distribution slot 82 includes two associated filament nozzles. As noted previously, each chamber may include from about 1 to 20, and in particular, from 2 to 10, and more particularly, from 2 to 4 associated filament nozzles.

Figure 8D:
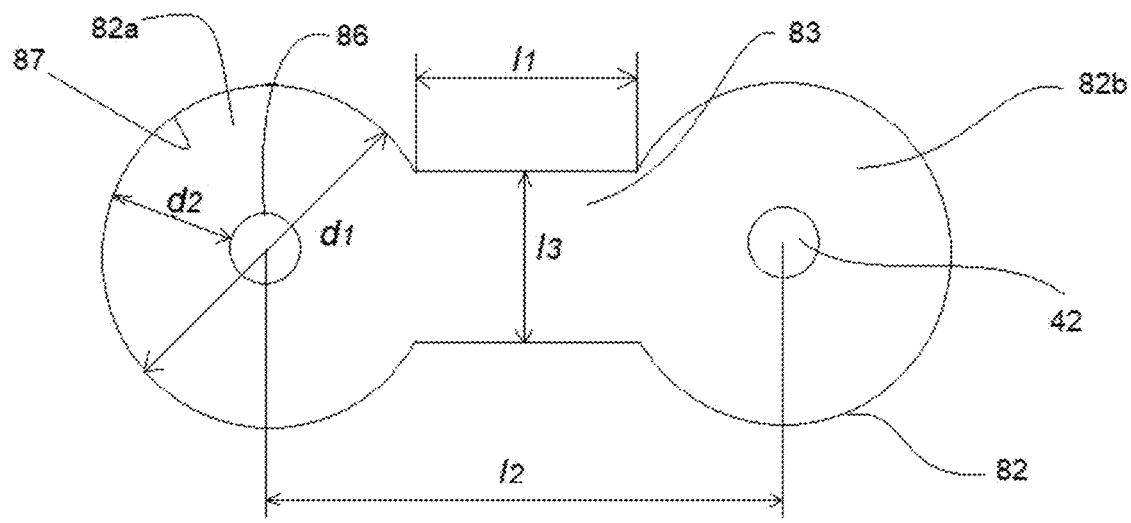

With reference to FIG. 8D, a gas distribution slot 82 comprising at least two chambers 82a, 82b, with a single filament nozzle 42 per chamber is shown.

In some embodiments the diameter d1 of each chamber 82a, 82b may range from 1.0 to 2.0 mm, with a diameter d1 of 1.2 to 1.6 mm being somewhat more preferred, and a diameter d1 of 1.3 to 1.5 mm being preferred, and diameter d1 of about 1.4 mm being even more preferred.

The air gap between the sidewall 86 of nozzle 42 and outerwall 87 of an individual chamber (e.g., 82a, 82b) in which the nozzle is disposed, may have a length (identified by reference character d2) that is from about 0.2 to 1.0 mm, and in particular, from about 0.3 to 0.9 mm, and more particularly, from about 0.2 to 0.4 mm, with a distance d2 from 0.25 to 0.4 being somewhat more typical.

In certain embodiments, the distance (identified by reference character l2) between the center of the filament nozzles 42 in each of the chambers 82a, 82b may range from about 1.3 to 3.5 mm, and in particular, from about 1.7 to 3.2 mm, and more particularly, from about 1.8 to 3.0 mm. In certain embodiments, the distance l2 may be from 1.9 to 2.2 mm, with a distance of 1.5 to 2.0 mm being somewhat preferred.

In certain embodiments, the length of channel 83 (identified by reference character l1) may range from about 0.9 to 2.6 mm, and in particular, from about 1.0 to 2.0 mm, and more particularly from about 1.1 to 1.5 mm being somewhat more typical.

The width of the fluid connecting channel 83 (identified by reference character l3) may range from about 0.4 to 1.6 mm, and in particular, from about 0.5 to 1.2 mm, and more particularly, from about 0.6 to 0.8 mm.

In certain embodiments, the ratio of the length of l1 to the width of l3 may be from about 1.3:2.6, and in particular, from about 1.5:1.3.

Figure 8E:
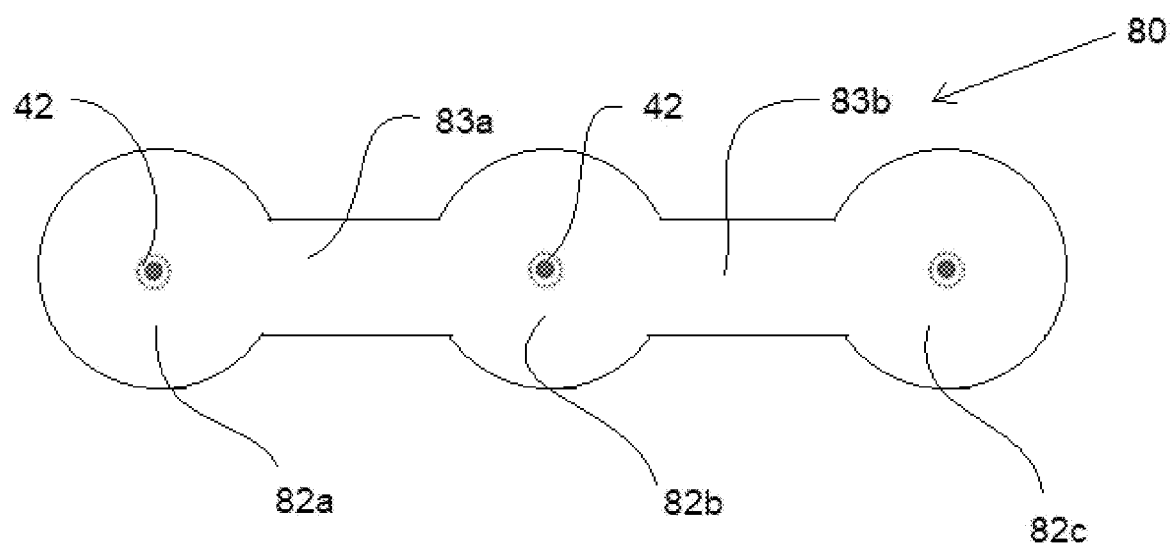
Figure 8F:
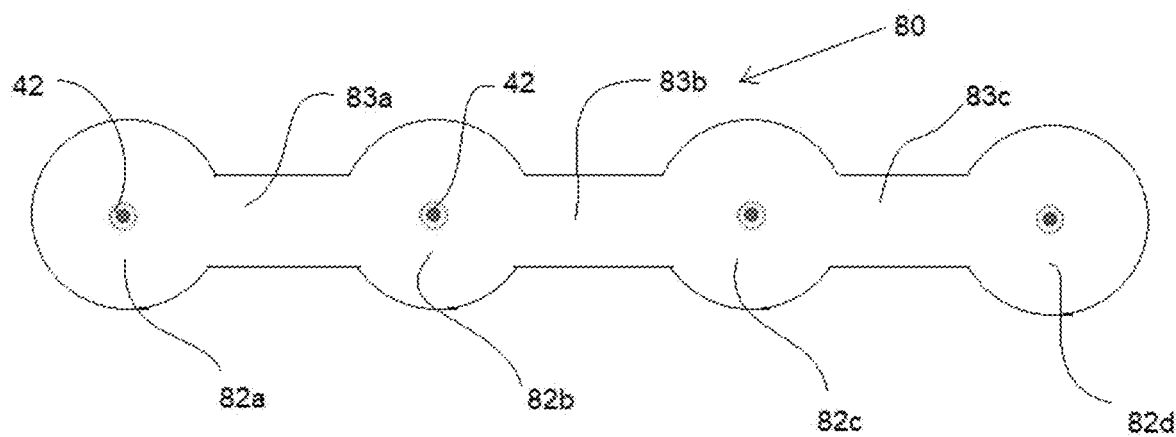

With reference to FIGS. 8E to 8F, variations of the gas distribution slots having dumb-bell like shapes are illustrated. In these embodiments, the gas distribution slots may include a plurality of successive chambers that are in fluid communication via fluid connecting channels. For example, FIG. 8E shows an embodiment having three chambers 82a, 82b, and 82c that are in fluid communication via fluid connecting channels 83a, 83b, and FIG. 8F shows an embodiment having four chambers 82a, 82b, 82c, and 82d that are in fluid communication via fluid connecting channels 83a, 83b, and 83c. The number of interconnected chambers in an individual gas distribution slot 80 may range from about 2 to 100, and in particular, from about 2 to 10, and more particularly, from about 2 to 6.

The dimensions of the gas distribution slots relative to the diameters of the chambers, air gap, length and width of the fluid connecting channels, and distances between the filament nozzles may be the same as those described above with respect to FIG. 8D.

As in the previously discussed embodiments, the gas distribution slots may extend longitudinally in the machine direction of the gas distribution plate, laterally in the cross direction of the gas distribution plate, or at some angle therebetween.

Figure 8G:
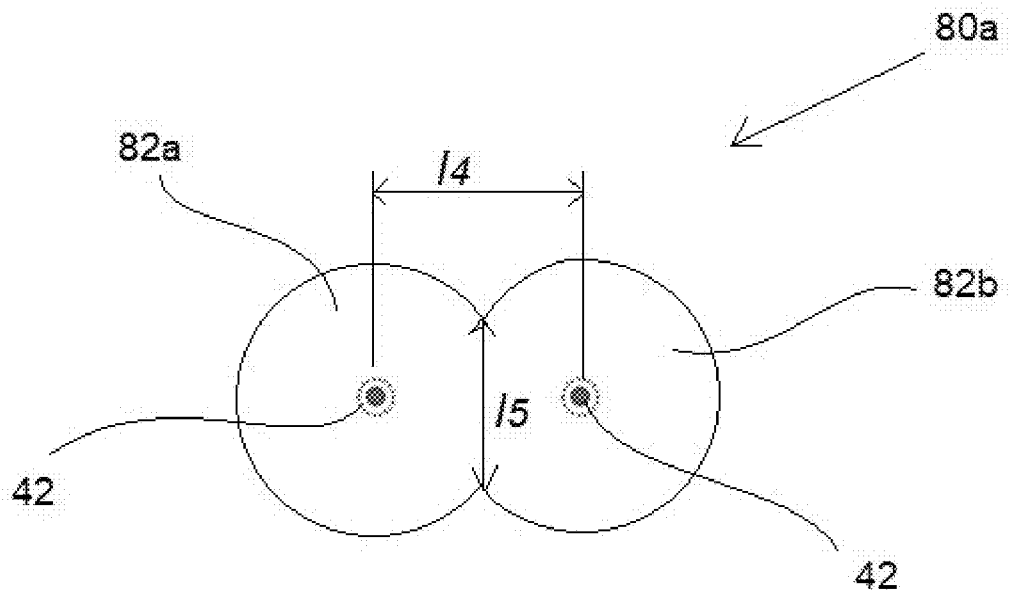

FIG. 8G illustrates an embodiment in which the immediately adjacent chambers of the gas distribution slot 80*a* converge and overlap. In the illustrated embodiment, the gas distribution slot 80*a* comprises two overlapping chambers 82*a*, 82*b*. In other embodiments, an individual gas distribution slot 80*a* may include a plurality of overlapping chambers, such as from about 2 to 100, and in particular, from about 2 to 10, and more particularly, from about 2 to 6. As in the previously discussed embodiments, the gas distribution slots may extend longitudinally in the machine direction of the gas distribution plate, laterally in the cross direction of the gas distribution plate, or at some angle therebetween.

The degree of overlap of surface area between the converging chambers may range from about 10 to 50 percent of the surface area of the chambers, with an overlap of surface area between 10 to 40 percent, and in particular 20 to 30 percent being preferred.

The lengths l4 between filament nozzles 42 in adjacent chambers may range from about 0.8 to 2.5 mm, and in particular, from about 1.2 to 2.2, and 1.8 to 2.0 mm being somewhat preferred.

The converging chambers define a pair of opposing inflection points having a distance l5 therebetween. The length of l5 will generally depend on the degree of overlap between the converging chambers. In certain embodiments, l5 has a length that is from about 0.4 to 1.6 mm, and in particular, from about 0.6 to 1.2 mm, and more particularly, from about 0.6 to 1.0 mm.

Although the chambers shown in FIGS. 8B-8G generally have a circular shape, it should be recognized that the chambers may have other shapes, such as oval, square, hexagonal, rectangular and the like.

Figure 8H:
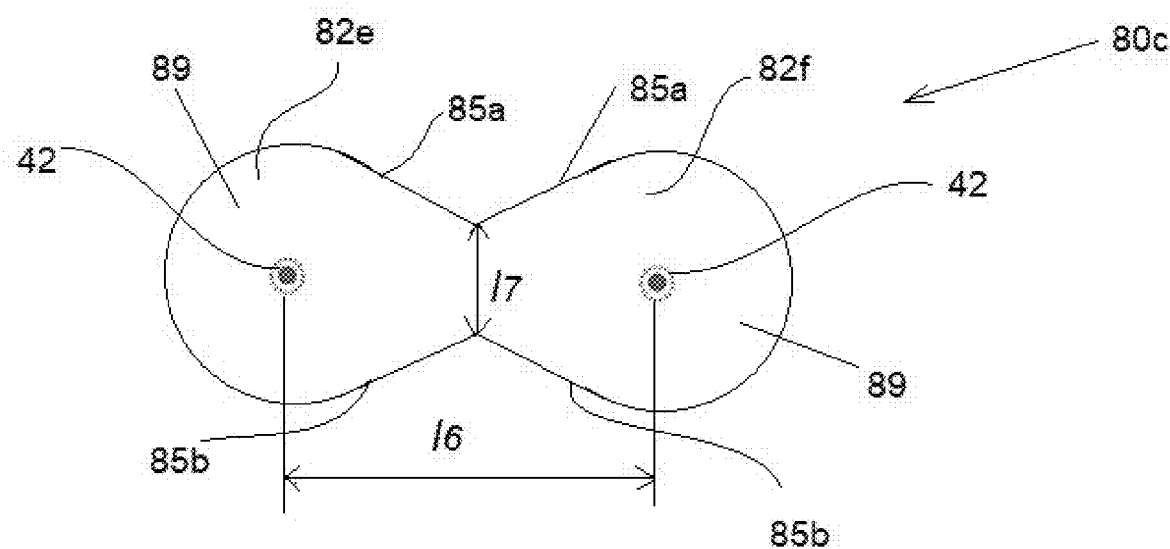

With reference to FIG. 8H, an embodiment of the gas distribution slot 80*c* is shown in which the gas distribution slot comprises a pair of converging chambers where each chamber has a tear drop or egg like shape. As shown, the individual chambers 82*e*, 82*f* have a tear drop or egg like shape in which each individual tear drop/egg shaped chamber includes a central chamber 89 and a pair of opposing sides 85*a*, 85*b* that extend from the peripheral edges of the central chamber and that converge towards a central point. In gas distribution slot 80*c*, the tear drop/egg shaped chambers 82*e*, 82*f* are configured and arranged so that the pair of opposing sides 85*a*, 85*b* of each adjacent chamber converge and overlap to define a minimum distance l7 between adjacent chambers 82*e*, 82*f*. The length of l7 will generally depend on the degree of overlap between the converging chambers. In certain embodiments, l5 has a length that is from about 0.4 to 1.6 mm, and in particular, from about 0.6 to 1.2 mm, and more particularly, from about 0.6 to 1.0 mm.

The lengths l6 between filament nozzles 42 in adjacent chambers may range from about 0.8 to 2.5 mm, and in particular, from about 1.2 to 2.2, and 1.8 to 2.0 mm being somewhat preferred.

The dimensions of the gas distribution slots 80*c* relative to the diameters of the chambers, air gap, length and distances between the filament nozzles may be the same as those described above with respect to FIG. 8D.

As in the previously discussed embodiments, the gas distribution slots may extend longitudinally in the machine direction of the gas distribution plate, laterally in the cross direction of the gas distribution plate, or at some angle therebetween.

Figure 8I:
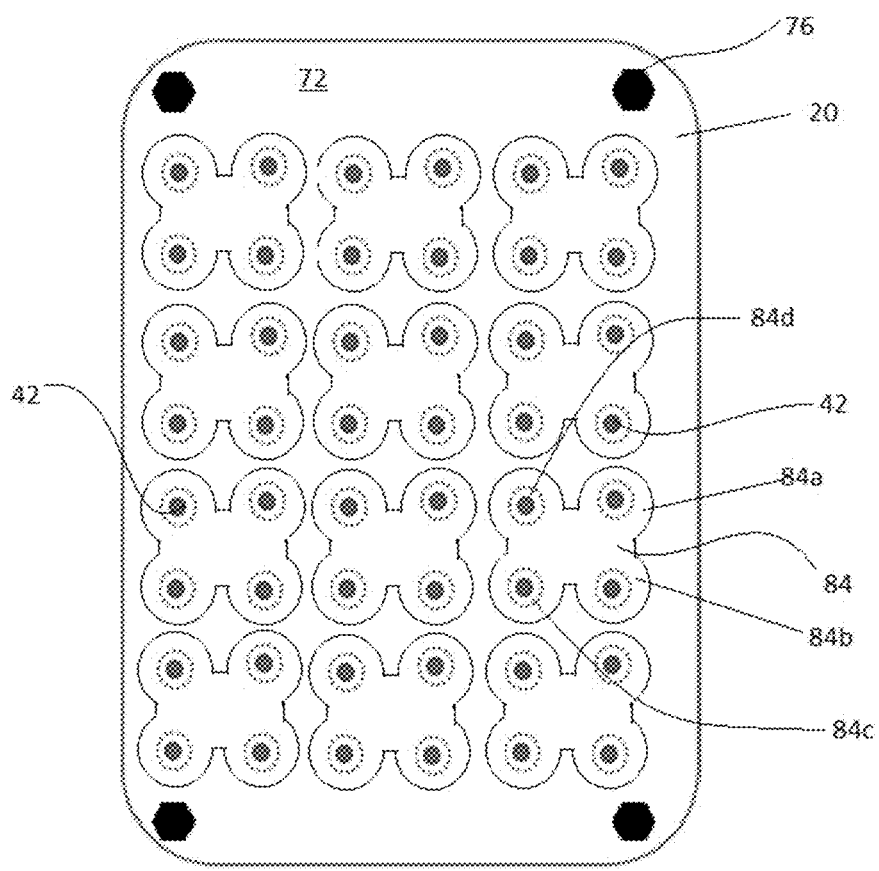

With reference to FIG. 8I, an embodiment of the assembled die block is shown in which the gas distribution plate 20 has a plurality of segmented gas distribution slots having a generally butterfly shape. In this embodiment, the segmented gas distribution slot 84 comprises four lobes 84*a*, 84*b*, 84*c*, 84*d* which each are associated with an individual filament nozzle 42.

As can be seen from the foregoing discussion, the gas distribution slots may have a wide variety of shapes and configurations. For example, in the embodiments depicted in FIGS. 5A-5D and 6A-6C, the gas distribution slot may be configured and arranged to receive an entire row/column of corresponding filament nozzles of the spinneret assembly. In other embodiments, the gas distribution slots may be segmented to accept only a portion of the filament nozzles in a corresponding row or column of the spinneret assembly. In some embodiments, the gas distribution slots may have other shapes and orientations, such as square, t-shaped, diagonal, lemniscate, dumb-bell, dog-bone, and the like relative to the rows/columns of the spinneret assembly.

Generally, each gas distribution slot is configured to receive at least two corresponding filament nozzles of the spinneret assembly. In some embodiments, the gas distribution slot may be configured to receive from about 2 to 10,000 individual filament nozzles, such as from about 4 to 5,000, and in particular, from about 100 to 3,000 individual filament nozzles.

With reference to FIGS. 9A and 9B, embodiments of the invention are shown in which the gas distribution plates 100*a*, 100*b*, respectively, include a combination of gas distribution slots 108*a*, 108*b*, 108*c*, and 108*d* and a plurality of individual gas distribution outlets 102 that are collectively associated with two or more filament nozzles 42. In particular, the gas distribution plate includes a plurality of filament apertures arranged in rows, each aperture configured to receive a single filament nozzle therein, and a plurality of gas distribution outlets arranged in rows. The rows of filament apertures and rows of gas distribution outlets define a pattern of alternating rows of filament nozzles and gas distribution outlets.

In the embodiment illustrated in FIG. 9A, the gas distribution plate includes four peripheral edges defining a generally rectangular shape. A pair of gas distribution slots are disposed towards opposite side edges of the distribution plate 100*a* (adjacent to opposite peripheral edges). The pattern of alternating rows of filament nozzles 106 and rows of gas distribution outlets 104 are disposed between the pair of opposing gas distribution slots 108*a*, 108*b*. The individual gas distribution outlets 102 are associated with two or more filament nozzles and cooperate with each other and the gas distribution slots 108*a*, 108*b* to form a shroud of pressurized gas that draws and attenuates the filaments extruded from the filament nozzles. In addition, the pair of gas distribution slots 108*a*, 108*b* extend along the length of the gas distribution plate (e.g., in the cross or machine direction) and help provide a continuous curtain of pressurized gas along the edges of the gas distribution plate.

In certain embodiments, the individual gas distribution outlets 102 have a generally circular shape defining an opening through which a stream of pressurized gas exits the gas distribution plate 100*a*. In other embodiments, the individual gas distribution outlets 102 may comprise other shapes, such as an oval, square, rectangle, and the like.

Turning to FIG. 9B, gas distribution plate 100b comprises four gas distribution slots 108a, 108b, 108c, and 108d that are disposed around the periphery of the gas distribution plate. In this embodiment, the gas distribution plate has four peripheral side edges defining a generally rectangular shape. A gas distribution slot is associated with each one of the side edges of the gas distribution plate 100b to form a curtain of pressurized gas that surrounds and envelopes the pattern of alternating rows of filament nozzles 106 and rows of gas distribution outlets 104.

Referring back to FIG. 6A, the width (w) of each gas distribution slot may range from about 0.5 to 100 mm, and in particular, from about 1 to 50 mm, and more particularly, from about 2 to 10 mm. In addition, the distance (x) between adjacent gas distribution slots typically ranges from about 1 to 25 mm, and in particular, from about 2 to 5 mm.

Referring again to FIGS. 5A, 6A, 7A, 7B, and 8A-8C one can see that each of the plurality of filament nozzles 42 within a corresponding gas distribution slot is preferably centrally aligned with respect to the sidewalls of the gas distribution slot. The reason for this is that the shroud of pressurized gas (air) provided by the gas distribution slot will then be evenly distributed around the outer periphery of the filament nozzles 42. Advantageously, it is believed that the pressurized gas (air) creates a curtain of gas that shrouds the plurality of filament nozzles 42 and assists in causing the extruded molten material 22 (polymer) to solidify and attenuate.

In addition, as the pressurized gas exits from each of the gas distribution slots, adjacent to the plurality of filament nozzles 42 at a predetermined velocity, the molten material (polymer) is extruded into filaments 22. Each of the plurality of filaments 22 within a given gas distribution slot is shrouded by the surrounding pressurized gas from filaments that are extruded from adjacent gas distribution slots to prevent roping. By "filament" it is meant a fine or thinly spun polymeric material still in a semi-soften state. By this arrangement, contact between adjacent filaments may be retarded or prevented.

The temperature of the pressurized gas (air) used in shrouding and attenuating the filaments 22 at or near the filament nozzles 42 can be at a lower temperature, the same temperature, or at a higher temperature, than the melt temperature of the passing filaments 22. Desirably, the temperature of the pressurized gas (air) used in shrouding and attenuating the filaments 22 at or near the filament nozzles 42 is at a temperature ranging from between about 0° C. to about 250° C. colder or hotter than the melt temperature of the filaments 22. More desirably, the temperature of the pressurized gas (air) used in shrouding and attenuating the filaments 22 at or near the filament nozzles 42 is at a temperature ranging from between about 0° C. to about 200° C. colder or hotter than the melt temperature of the filaments 22. Even more desirably, the temperature of the pressurized gas (air) used in shrouding and attenuating the filaments 22 at or near the nozzles 42 is at a temperature ranging from between about 0° C. to about 150° C. colder or hotter than the melt temperature of the filaments 22. Most desirably, the temperature of the pressurized gas (air) used in shrouding and attenuating the filaments 22 at or near the filament nozzles 42 is at a temperature ranging from between about 0° C. to about 100° C. colder or hotter than the melt temperature of the filaments 22.

With reference to FIG. 10, a cross-sectional view of the assembled spinneret and gas distribution plate is shown and designated by reference character 110. As shown, the gas distribution plate 20 comprises a plurality of spaced apart gas distribution slots 70 that extend laterally through the gas distribution plate. In the illustrated embodiment, the gas distribution slots 70 extend in the cross direction of the spin beam. Similarly, the rows of filament nozzles 42 also extend in the cross direction of the spin beam. In FIG. 10, only a single filament nozzle 42 is shown although in practice it would be expected that each gas distribution slot 70 would include a corresponding row comprising a plurality of spaced apart filament nozzles.

Each of the gas distribution slots 70 include a plurality of sidewalls 73 that collectively define the gas distribution slot. In the case of a rectangular shaped gas distribution slot, the slot will comprise four sidewalls 73. The tubular body 46 of the filament nozzle 42 extends downwardly from the spinneret assembly 44, through the gas distribution slot 70, and below the lower surface 72 of the gas distribution plate 20. As shown, the distal end 50 of the filament nozzle 42 is disposed below the lower surface of the gas distribution plate.

The tubular body 46 of the filament nozzle 42 includes sidewall 47. In certain embodiments, the sidewalls 73 of the gas distribution slot 70 and the sidewall 47 of the tubular body 46 are parallel or substantially parallel to each other. As a consequence, when a stream of gas supplied by the gas supply manifold 78 is introduced into the gas distribution slot, the stream of fills the gas distribution slot and also surrounds the tubular bodies 46 of the filament nozzles. The stream of gas flows downwardly towards the distal ends 50 of the filament nozzles. As the stream of gas exits the lower outlet 75 of the gas distribution slot, the stream of gas is flowing in a direction that is parallel or substantially parallel to the direction in which the filaments 22 are extruded from the filament nozzles. The parallel or substantially parallel flow of the gas stream results in the gas stream contacting the surface of the filaments at a contact angle that is less than 5°, and preferably, less than 1°.

In certain embodiments of the invention, the gas distribution plate is configured and arranged so that the stream of gas exits outlet of the gas distribution slot at an angle that is not parallel or substantially parallel to the outer surfaces of the filament nozzles. In this regard, FIG. 11A illustrates a cross-sectional view of an assembled spinneret and gas distribution plate is shown. FIG. 11A shows a variety of representative configurations of gas distribution slots in which the sidewalls of the gas distribution slot are angled relative to the extrusion direction of the filaments 22.

The first configuration, identified by reference character 79a, includes a gas distribution slot 70 having two sidewalls 73 that extend laterally in the cross direction of the spin beam. As in the embodiment depicted in FIG. 10, each of the gas distribution slots 70 include a plurality of sidewalls 73 that collectively define the gas distribution slot. In the case of a rectangular shaped gas distribution slot, the slot will comprise four sidewalls 73. The body 46 of the filament nozzle 42 extends downwardly from the spinneret assembly 44 and at least partially into the gas distribution slot 70. The distal ends 50 of the filament nozzles 42 are located adjacent to the lower outlet of the gas distribution slot 70. In this embodiment, the sidewalls 73 of the gas distribution slot are shown as being parallel or substantially parallel to the sidewall 47 of the filament nozzle's tubular body 46. To create a non-parallel angle relative to the direction of extrusion of the filaments, a pair of angled blocks 77 are attached to opposite sidewalls 73 to create angle <a (the angle between the upper surface of the block and the outer surface of the tubular body 46). Preferably, the pair of angled blocks 77 extend laterally in the cross direction of the spin beam for the entire length of the gas distribution slot.

In certain embodiments, <a is greater than 5°, greater than 10°, greater than 15°, greater than 20°, greater than 25°, greater than 30°, greater than 35°, greater than 40°, greater than 45°, greater than 50°, greater than 55°, or greater than 60°. For example, <a may range from about 5° to 75°, from about 10° to 70°, from about 15° to 65°, from about 20° to 60°, from about 25° to 55°, and from about 30° to 50°. In a preferred embodiment, <a is from about 30° to 45°.

With respect to the configuration identified by reference character 79b, the filament nozzle 42 is partially disposed within the gas distribution slot 70. The lower portion 81 of the gas distribution slot includes a pair of beveled sidewalls 73 that are angled relative to the sidewall 47 of the tubular body 46. The distal end 50 of the filament nozzle 42 is depicted as being positioned adjacent to the upper end of the lower portion 81 of the gas distribution slot. In this embodiment, the molten polymer is extruded from the distal end of the filament nozzle while still within the gas distribution slot to form filament 22. The gas stream within the gas distribution slot attenuates and draws the filaments as they are discharged from the lower outlet of the gas distribution slot.

Turning now to the third configuration, designated by reference character 79c, the distal ends 50 of the filament nozzles 42 are positioned adjacent or in proximity to the lower surface 72 of the gas distribution plate 20. As in the previously discussed embodiment, the lower portion of the gas distribution slot includes a pair of opposing beveled sidewalls 73 that are angled relative to the sidewall 47 of the tubular body 46.

As in the configuration designated by reference character 79a, discussed above, the angle between the sidewall 47 of the tubular body 46 and the beveled sidewalls 73 of configurations 79b, 79c, may be greater than 5°, greater than 10°, greater than 15°, greater than 20°, greater than 25°, greater than 30°, greater than 35°, greater than 40°, greater than 45°, greater than 50°, greater than 55°, or greater than 60°. For example, the angle may range from about 5° to 75°, from about 10° to 70°, from about 15° to 65°, from about 20° to 60°, from about 25° to 55°, and from about 30° to 50°. In a preferred embodiment, the angle between the beveled sidewall 73 and the sidewall 47 of the tubular body 46 is from about 30° to 45°.

During filament formation, a stream of gas is introduced into the gas distribution slots via gas supply manifold 78. The stream of gas fills the distribution slot and flows in the direction of the lower outlet of the gas distribution slot. The beveled sidewalls result in the gas contacting the exterior surface of the filaments at an angle that is non-parallel or substantially non-parallel. In certain embodiments, the stream of gas contacts the surface of the filaments at an angle that is greater than 5°, greater than 10°, greater than 15°, greater than 20°, greater than 25°, greater than 30°, greater than 35°, greater than 40°, greater than 45°, greater than 50°, greater than 55°, or greater than 60°. For example, the angle of contact may range from about 5° to 75°, from about 10° to 70°, from about 15° to 65°, from about 20° to 60°, from about 25° to 55°, and from about 30° to 50°. In a preferred embodiment, the angle of contact is from about 30° to 45°.

FIG. 11B illustrates a further embodiment of the invention in which the gas distribution slots 70 include a pair of opposing sidewalls 73a, 73b that are angled relative to the sidewall 47 of the tubular body 46. In this embodiment, a pair of opposing gas distribution nozzles 77a, 77b are disposed on opposing sidewalls 73a, 73b, respectively, and are configured to direct opposing streams of gas 81a, 81b towards extruded filament 22. The opposing pair of gas distribution nozzles 77a, 77b may be in fluid communication with gas distribution manifold 78 via gas inlet channels 78a.

The angle between the sidewall 47 of the tubular body 46 and the opposing sidewalls 73a, 73b may be greater than 5°, greater than 10°, greater than 15°, greater than 20°, greater than 25°, greater than 30°, greater than 35°, greater than 40°, greater than 45°, greater than 50°, greater than 55°, or greater than 60°. For example, the angle may range from about 5° to 75°, from about 10° to 70°, from about 15° to 65°, from about 20° to 60°, from about 25° to 55°, and from about 30° to 50°.

In one embodiment, an angle β formed between the sidewall 73a of the gas distribution slot 70 and a line ("$\ell$") parallel or substantially parallel to the lower surface 72 of distribution plate is from about 30° to 50°.

As discussed previously, the distal ends of the filament nozzles may extend downwardly below the lower surface of the gas distribution plate, be substantially coplanar with the lower surface of the gas distribution plate, or partially extend through the gas distribution slots of the gas distribution plate. In this regard, FIGS. 12A-12C illustrate various configurations of the filament nozzles relative to the gas distribution plate.

FIG. 12A illustrates an embodiment in which the distal ends 50 of the filament nozzles 42 extend downwardly below the lower surface 72 of the gas distribution plate 20. In particular, the plurality of filament nozzles 42 extend from the spinneret assembly 44 and into gas distribution slots 70 and at least a portion of the distal end 50 of the of the filament nozzle is disposed below the lower surface of the gas distribution plate. FIG. 12B illustrates an embodiment in which the distal ends 50 of the filament nozzles 42 are coplanar or substantially coplanar with the lower surface 72 of the gas distribution plate 20. FIG. 12C illustrates an embodiment in which the distal ends 50 of the filament nozzles 42 extend partially through the gas distribution channel 70 and do not extend below the lower surface 72 of the gas distribution plate 20.

II. Representative Inventive Nonwoven Fabrics

Nonwoven fabrics prepared in accordance with embodiments of the invention may be used in wide variety of articles and applications. For instance, embodiments of the invention may be used for personal care applications, for example products for babycare (diapers, wipes), for femcare (pads, sanitary towels, tampons), for adult care (incontinence products), or for cosmetic applications (pads), agricultural applications, for example root wraps, seed bags, crop covers, industrial applications, for example work wear coveralls, airline pillows, automobile trunk liners, sound proofing, and household products, for example mattress coil covers and furniture scratch pads. In a preferred embodiment, nonwoven fabrics may be used for the manufacture of absorbent wipes.

In certain embodiments, the nonwoven fabrics in accordance with embodiments of the invention may have a basis weight ranging from about 8 to 65 grams per square meter (gsm), and in particular, from about 10 to 40 gsm. In a preferred embodiment, the nonwoven fabric has a basis weight of about 15 to 30 gsm.

Nonwoven fabrics in accordance with embodiments of the invention may be prepared with a wide variety of different polymers and polymeric blends. Examples of suitable polymers for preparing the fibers include polyolefins, such as polypropylene and polyethylene, and copolymers thereof, polyesters, such as polyethylene terephthalate (PET), polytrimethylene terephthalate (PTT), and polybutylene terephthalate (PBT), nylons, polystyrenes, polyurethanes, copolymers, and blends thereof, and other synthetic polymers that may be used in the preparation of fibers. In some embodiment, the polymer can be selected from the group consisting of: polyolefins, polyesters, polyethylene terephthalates, polybutylene terephthalates, polycyclohexylene dimethylene terephthalates, polytrimethylene terephthalates, polymethyl methacrylates, polyamides, nylons, polyacrylics, polystyrenes, polyvinyls, polytetrafluoroethylenes, ultrahigh molecular weight polyethylenes, very high molecular weight polyethylenes, high molecular weight polyethylenes, polyether ether ketones, non-fibrous plasticized celluloses, polyethylenes, polypropylenes, polybutylenes, polymethylpentenes, low-density polyethylenes, linear low-density polyethylenes, high-density polyethylenes, polystyrenes, acrylonitrile-butadiene-styrenes, styrene-acrylonitriles, styrene tri-block and styrene tetra block copolymers, styrene-butadienes, styrene-maleic anhydrides, ethylene vinyl acetates, ethylene vinyl alcohols, polyvinyl chlorides, cellulose acetates, cellulose acetate butyrates, plasticized cellulosics, cellulose propionates, ethyl cellulose, natural fibers, any derivative thereof, any polymer blend thereof, any copolymer thereof or any combination thereof.

In some embodiments, the polymers may be extensible and/or elastic.

In some embodiments, the polymers may comprise polymers derived from mechanically or chemically recycled feedstocks. For example, up to 100% of the polymer comprising the nonwoven fabric may be derived from recycled polymers.

In further embodiments, nonwoven fabrics nonwoven fabrics in accordance with one or more embodiments of the invention may be prepared from sustainable polymers. In contrast to polymers derived from petroleum sources, sustainable polymers are generally derived from a bio-based material. In some embodiments, a sustainable polymer may also be considered biodegradeable. A special class of biodegradable product made with a bio-based material might be considered as compostable if it can be degraded in a composting environment. The European standard EN 13432, "Proof of Compostability of Plastic Products" may be used to determine if a fabric or film comprised of sustainable content could be classified as compostable.

In one such embodiment, the nonwoven fabric comprises fibers comprising a sustainable polymer. In certain embodiments, the fibers are substantially free of synthetic materials, such as petroleum-based materials and polymers. For example, fibers comprising the nonwoven fabric may have less than 25 weight percent of materials that are non-bio-based, and more preferably, less than 20 weight percent, less than 15 weight percent, less than 10 weight percent, and even more preferably, less than 5 weight percent of non-bio-based materials, based on the total weight of the nonwoven fabric.

In one embodiment, sustainable polymers for use may include aliphatic polyester based polymers, such as polylactic acid, and bio-based derived polyethylene.

Aliphatic polyesters useful in the present invention may include homo- and copolymers of poly(hydroxyalkanoates), and homo- and copolymers of those aliphatic polyesters derived from the reaction product of one or more polyols with one or more polycarboxylic acids that are typically formed from the reaction product of one or more alkanediols with one or more alkanedicarboxylic acids (or acyl derivatives). Polyesters may further be derived from multifunctional polyols, e.g. glycerin, sorbitol, pentaerythritol, and combinations thereof, to form branched, star, and graft homo- and copolymers. Polyhydroxyalkanoates generally are formed from hydroxyacid monomeric units or derivatives thereof. These include, for example, polylactic acid, polyhydroxybutyrate, polyhydroxyvalerate, polycaprolactone and the like. Miscible and immiscible blends of aliphatic polyesters with one or more additional semicrystalline or amorphous polymers may also be used.

One useful class of aliphatic polyesters are poly(hydroxyalkanoates), derived by condensation or ring-opening polymerization of hydroxy acids, or derivatives thereof. Suitable poly(hydroxyalkanoates) may be represented by the formula: $H(O-R-C(O)-)_n OH$ where R is an alkylene moiety that may be linear or branched having 1 to 20 carbon atoms, preferably 1 to 12 carbon atoms optionally substituted by caternary (bonded to carbon atoms in a carbon chain) oxygen atoms; n is a number such that the ester is polymeric, and is preferably a number such that the molecular weight of the aliphatic polyester is at least 10,000, preferably at least 30,000, and most preferably at least 50,000 daltons. In certain embodiments, the molecular weight of the aliphatic polyester is typically less than 1,000,000, preferably less than 500,000, and most preferably less than 300,000 daltons. R may further comprise one or more caternary (i.e. in chain) ether oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydropentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e. polyglycolide). Copolymers of two or more of the above hydroxy acids may also be used, for example, poly(3-hydroxybutyrate-co-3-hydroxyvalerate), poly(lactate-co-3-hydroxypropanoate), poly(glycolide-co-p-dioxanone), and poly(lactic acid-co-glycolic acid). Blends of two or more of the poly(hydroxyalkanoates) may also be used, as well as blends with one or more semicrystalline or amorphous polymers and/or copolymers.

The aliphatic polyester may be a block copolymer of poly(lactic acid-co-glycolic acid). Aliphatic polyesters useful in the inventive compositions may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general formula:

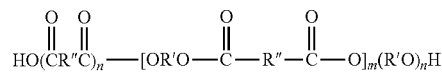

where R' and R'' each represent an alkylene moiety that may be linear or branched having from 1 to 20 carbon atoms, preferably 1 to 12 carbon atoms, and m is a number such that the ester is polymeric, and is preferably a number such that the molecular weight of the aliphatic polyester is at least 10,000, preferably at least 30,000, and most preferably at least 50,000 daltons, but less than 1,000,000, preferably less than 500,000 and most preferably less than 300,000 daltons. Each n is independently 0 or 1. R' and R" may further comprise one or more caternary (i.e. in chain) ether oxygen atoms.

Examples of aliphatic polyesters include those homo- and copolymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; polyethylene glycol; 1,2-propanediol; 1,3-propanediol; 1,2-propanediol; 1,2-butanediol; 1,3-butanediol; 1,4-butanediol; 2,3-butanediol; 1,6-hexanediol; 1,2 alkane diols having 5 to 12 carbon atoms; diethylene glycol; polyethylene glycols having a molecular weight of 300 to 10,000 daltons, and preferably 400 to 8,000 daltons; propylene glycols having a molecular weight of 300 to 4000 daltons; block or random copolymers derived from ethylene oxide, propylene oxide, or butylene oxide; dipropylene glycol; and polypropylene glycol, and (c) optionally a small amount, i.e., 0.5-7.0 mole percent of a polyol with a functionality greater than two, such as glycerol, neopentyl glycol, and pentaerythritol.

Such polymers may include polybutylene succinate homopolymer, polybutylene adipate homopolymer, polybutyleneadipate-succinate copolymer, polyethylenesuccinate-adipate copolymer, polyethylene glycol succinate homopolymer and polyethylene adipate homopolymer.

Commercially available aliphatic polyesters include poly(lactide), poly(glycolide), poly(lactide-co-glycolide), poly(L-lactide-co-trimethylene carbonate), poly(dioxanone), poly(butylene succinate), and poly(butylene adipate).

The term "aliphatic polyester" covers—besides polyesters which are made from aliphatic and/or cycloaliphatic components exclusively also polyesters which contain besides aliphatic and/or cycloaliphatic units, aromatic units, as long as the polyester has substantial sustainable content.

In addition to PLA based resins, nonwoven fabrics in accordance with embodiments of the invention may include other polymers derived from an aliphatic component possessing one carboxylic acid group and one hydroxyl group, which are alternatively called polyhydroxyalkanoates (PHA). Examples thereof are polyhydroxybutyrate (PHB), poly-(hydroxybutyrate-co-hydroxyvaleterate) (PHBV), poly-(hydroxybutyrate-co-polyhydroxyhexanoate) (PHBH), polyglycolic acid (PGA), poly-(epsilon-caprolactone) (PCL) and preferably polylactic acid (PLA).

Examples of additional polymers that may be used in embodiments of the invention include polymers derived from a combination of an aliphatic component possessing two carboxylic acid groups with an aliphatic component possessing two hydroxyl groups, and are polyesters derived from aliphatic diols and from aliphatic dicarboxylic acids, such as polybutylene succinate (PBSU), polyethylene succinate (PESU), polybutylene adipate (PBA), polyethylene adipate (PEA), polytetramethy-lene adipate/terephthalate (PTMAT).

Useful aliphatic polyesters include those derived from semicrystalline polylactic acid. Poly(lactic acid) or polylactide (PLA) has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly(lactide), while the poly(lactide) derived from the D,L-lactide is amorphous.

Generally, polylactic acid based polymers are prepared from dextrose, a source of sugar, derived from field corn. In North America corn is used since it is the most economical source of plant starch for ultimate conversion to sugar. However, it should be recognized that dextrose can be derived from sources other than corn. Sugar is converted to lactic acid or a lactic acid derivative via fermentation through the use of microorganisms. Lactic acid may then be polymerized to form PLA. In addition to corn, other agriculturally-based sugar sources may be used including rice, sugar beets, sugar cane, wheat, cellulosic materials, such as xylose recovered from wood pulping, and the like.

The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, at least 90% of one isomer, or at least 95% of one isomer in order to maximize the crystallinity.

In some embodiments, an approximately equimolar blend of D-polylactide and L-polylactide is also useful. This blend forms a unique crystal structure having a higher melting point (about 210° C.) than does either the D-poly(lactide) and L-(polylactide) alone (about 190° C.), and has improved thermal stability.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-beta-methylvaleric acid, alpha-hydroxyoctanoic acid, alpha-hydroxydecanoic acid, alpha-hydroxymyristic acid, and alpha-hydroxystearic acid.

Blends of poly(lactic acid) and one or more other aliphatic polyesters, or one or more other polymers may also be used. Examples of useful blends include poly(lactic acid) and poly(vinyl alcohol), polyethylene glycol/polysuccinate, polyethylene oxide, polycaprolactone and polyglycolide.

In certain preferred embodiments, the aliphatic polyester component comprises a PLA based resin. A wide variety of different PLA resins may be used to prepare nonwoven fabrics in accordance with embodiments of the invention. The PLA resin should have proper molecular properties to be spun in spunbond processes. Examples of suitable include PLA resins are supplied from NatureWorks LLC, of Minnetonka, Minn. 55345 such as, grade 6752D, 6100D, and 6202D, which are believed to be produced as generally following the teaching of U.S. Pat. Nos. 5,525,706 and 6,807,973 both to Gruber et al. Other examples of suitable PLA resins may include L130, L175, and LX175, all from Corbion of Arkelsedijk 46, 4206 A C Gorinchem, the Netherlands.

In some embodiments, the inventive nonwoven fabrics may comprise sustainable polymer components of biodegradable products that are derived from an aliphatic component possessing one carboxylic acid group (or a polyester forming derivative thereof, such as an ester group) and one hydroxyl group (or a polyester forming derivative thereof, such as an ether group) or may be derived from a combination of an aliphatic component possessing two carboxylic acid groups (or a polyester forming derivative thereof, such as an ester group) with an aliphatic component possessing two hydroxyl groups (or a polyester forming derivative thereof, such as an ether group).

Additional nonlimiting examples of bio-based polymers include polymers directly produced from organisms, such as polyhydroxyalkanoates (e.g., poly(beta-hydroxyalkanoate), poly(3-hydroxybutyrate-co-3-hydroxyvalerate, NODAX™), and bacterial cellulose; polymers extracted from plants and biomass, such as polysaccharides and derivatives thereof (e.g., gums, cellulose, cellulose esters, chitin, chitosan, starch, chemically modified starch), proteins (e.g., zein, whey, gluten, collagen), lipids, lignins, and natural rubber; and current polymers derived from naturally sourced monomers and derivatives, such as bio-polyethylene, bio-polypropylene, polytrimethylene terephthalate, polylactic acid, NYLON 11, alkyd resins, succinic acid-based polyesters, and bio-polyethylene terephthalate.

In some embodiments, the bio-based polymer may comprise bio-based polyethylene that is derived from a biological source. For example, bio-based polyethylene can be prepared from sugars that are fermented to produce ethanol, which in turn is dehydrated to provide ethylene. An example of a suitable sugar cane derived polyethylene is available from Braskem S.A. under the product name PE SHA7260.

In some embodiments, the filaments may include one or more additives that are blended with the polymer(s) during the melt extrusion phase. Examples of suitable additives include one or more of colorants, such as pigments (e.g., $TiO_2$), UV stabilizers, hydrophobic agents, hydrophilic agents, antistatic agent, elastomers, compatibilizers antioxidants, anti-block agent, slip agent, optical brighteners, flame retardants, antimicrobials, such as copper oxide and zinc oxide and the like.

III. Apparatus and Process for Preparing Fibrous Nonwoven Fabrics

In a further aspect, an apparatus and process is provided for preparing a fibrous nonwoven fabric comprising a mixture of thermoplastic filaments and a plurality of solid additives, such as wood pulp fibers. In particular, the thermoplastic filaments may be prepared using a spin beam in accordance with one or more embodiments of the invention.

With reference to FIG. 13, a system 200 and associated method is shown for producing a composite nonwoven fabric 212 comprising a blend of thermoplastic filaments and a plurality of solid additives. The composite fabric 212 can have a high loft. The composite fabric 212 is a matrix formed by introducing a stream of fibers of a first material 214 between two polymer streams. By "matrix" it is meant a situation or surrounding substance within which something else originates, develops or is contained. The first material 214 comprises a solid additive and can be absorbent fibers or non-absorbent fibers. The first material 214 can be in the form of fibers, particles, gels, etc. In certain embodiments, the first material 214 includes staple/pulp fibers.

The first material 214 can include fibers formed by a variety of pulping processes, such a kraft pulp, sulfite pulp, thermo-mechanical pulp, etc. Suitable pulps include treated and untreated pulps. The pulp fibers may include softwood fibers having an average fiber length of greater than 1 millimeter (mm) and particularly from about 2 mm to 5 mm. Such softwood fibers can include, but are not limited to: northern softwood, southern softwood, redwood, red cedar, hemlock, pine (e.g. southern pines), spruce (e.g. black spruce), combinations thereof, and so forth. Exemplary commercially available pulp fibers suitable in the present invention include those available from Weyerhaeuser Co. of Federal Way, Washington under the designation "Weyco CF-405". Hardwood fibers, such as *eucalyptus*, maple, birch, aspen, and so forth, can also be used. In certain instances, *eucalyptus* fibers may be particularly desired to increase the softness of the hybrid non-woven web. *Eucalyptus* fibers can also enhance the brightness, increase the opacity, and change the pore structure of the hybrid non-woven web to increase its wicking ability. Moreover, if desired, secondary fibers obtained from recycled materials may be used, such as fiber pulp from sources such as, for example, newsprint, reclaimed paperboard and office waste.

Further, other natural fibers can also be used in the present invention, such as abaca, sabai grass, milkweed floss, pineapple leaf, and so forth. In addition, in some instances, synthetic fibers can also be utilized. Additional fibers include cotton fibers and cotton linters in whole or blends with the foregoing discussed natural fibers.

In certain embodiments, the solid additives of the first material compromise natural fibers. Generally, natural fibers are derived from plants or animals. Natural fibers derived from plants typically comprise cellulose materials, and may include cotton fibers, cotton linters, flax fibers, hemp fibers, grass fibers, such as elephant grass, jute fibers, abaca fibers, coir fibers, ramie fibers (also known as Chinese grass), sisal fibers, and the like.

In certain embodiments, the first material 214 may comprise a pulp derived from bamboo.

In addition, natural fibers derived from animals may include wool, silk, camel hair, alpaca wool, cashmere, angora wool, and the like. In a preferred embodiment, the natural fibers comprise cotton fibers.

In certain embodiments, the solid additive may comprise a blend of cellulose fibers and non-cellulose fibers.

A wide variety of different cellulose materials may be used for the cellulose fibers. Fibers from Esparto grass, bagasse, kemp, flax, and other lignaceous and cellulose fiber sources may be utilized. Other fibers include absorbent natural fibers made from regenerated cellulose, polysaccharides or other absorbent fiber-forming compositions. In certain embodiments, the natural fibers comprise non-bleached cotton fibers having fiber lengths ranging from about 15 to 38 mm.

When present, suitable materials for the non-cellulose fibers for as the solid additive may comprise monocomponent or multicomponent fibers, or mixtures of moncomponent and multicomponent fibers. In a preferred embodiment, the non-cellulose fibers comprise bicomponent fibers having a sheath/core configuration.

In some embodiments, the solid additive may comprise staple fibers. Staple fibers typically have lengths ranging from about 10 to 65 mm, and in particular, from about 20 to 15 mm, and more particularly, from about 25 to 50 mm.

Besides or in conjunction with pulp fibers, the first material 214 may also include a superabsorbent that is in the form of fibers, particles, gels, etc. Generally speaking, superabsorbents are water-swellable materials capable of absorbing may times their weight in fluids. The superabsorbent may be formed from natural, synthetic and modified natural polymers and materials. Examples of synthetic superabsorbent polymers include the alkali metal and ammonium salts of poly(acrylic acid) and poly(methacrylic acid), poly(acrylamides), poly(vinyl ethers), maleic anhydride copolymers with ethers and alpha-olefins, poly(vinyl pyrrolidone), poly(vinylmorpholinone), poly(vinyl alcohol), and mixtures and copolymers thereof. Further superabsorbents include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and so forth. Mixtures of natural and wholly or partially synthetic superabsorbent polymers may also be useful in the present invention. Particularly suitable superabsorbent polymers are HYSORB 8800AD, available from BASF of Charlotte, N.C., and FAVOR SXM 9300, available from Degrussa Superabsorber of Greensboro, N.C. In addition, natural super absorbents may be used, such as Glucomannan. When present, the natural superabsorbent may comprise 100% of the superabsorbent, or may be blended with synthetic super absorbents.

Still referring to FIG. 13, the first material 214 can enter the system or process 200 in the form of sheets or mats 216 which are fed into a fiberizer 218. The fiberizer 218 can vary in size, shape and design. The fiberizer 218 functions to break the sheets or mats 218 into a plurality of individual fibers 214. The fiberizer 218 can vary. For example, the fiberizer 218 can be a hammer mill, disk mill, a picker roll, or some other mechanism known to those skilled in the art. The fiberizer 218 contains a discharge nozzle 220 that delivers the fiberized pulp fibers between two filament streams, 242 and 262. The discharge nozzle 220 can be designed according to the teachings of U.S. Pat. No. 8,122,570 issued to Jezzi on Feb. 28, 2012 in order to deliver uniform pulp fibers across the width of the machine. This patent is incorporated by reference and made a part hereof. Alternatively, the solid additives, such as pulp fibers, may be manually introduced or introduced directly from pre-opened bales, rolls, bags, boxes, and the like.

The throughput of the first material 214 can be controlled by the input feeding speed of the rolls, sheets or mats 216, as well as by the gas (air) blower speed of a blower connected to the fiberizer 218 or the nozzle 220. Because of the high strength of the fibers of the first and second filament streams 240 and 262 respectively, which will be discussed below, the final concentration of the fibers of the first material 214 in the hybrid, non-woven web 12 can range from between about 10% to about 60%. Desirably, the final concentration of the fibers of the first material 214 in the composite fabric 212 can range from between about 15% to about 50%. More desirably, the final concentration of the fibers of the first material 214 in the composite fabric 212 can range from between about 20% to about 40%. Even more desirably, the final concentration of the fibers of the first material 214 in the composite fabric 212 can range from between about 25% to about 35%.

The individual fibers 214 are conveyed downward through the nozzle 220. A gas, such as air, is supplied to the upper end of the nozzle 220 to serve as a medium for conveying the fibers of the first material 214 through the nozzle 220.

The gas (air) may be supplied by any conventional arrangement such as, for example, an air blower (not shown).

It is envisioned that other materials, such as an additive, may be added to or be entrained in the gas (air) stream to treat the fibers of the first material 214, if desired. The individual fibers of the first material 214 are typically conveyed through the nozzle 220 at about the velocity at which the fibers of the first material 214 leave the fiberizer 218. In other words, the fibers of the first material 214 that enter the nozzle 220 generally maintain their velocity in both magnitude and direction. U.S. Pat. No. 4,100,324, issued to Anderson et al. teaches such an arrangement and is incorporated by reference and made a part hereof.

Still referring to FIG. 13, a first polymer resin 222, in the form of small solid pellets, granules or powder, is placed into a hopper 224 and is then routed through a conduit 226 to an extruder 228. In the extruder 228, the first polymer resin 222 is heated to an elevated temperature. The temperature will vary depending on the composition and melting point of a particular polymer. Usually, the first polymer resin 222 is heated to a temperature at or above its melt temperature. The molten, first polymer resin 222 is transformed into a molten material (polymer) which is then routed through a conduit 230 to spin beam 232. Spin beam 232 is in accordance with the spin beam discussed above with respect to FIGS. 1 and 2 (see reference character 16) having a spinneret assembly (see FIG. 4, reference character 44) and a gas distribution plate (see FIGS. 5B, 6A, 8A-8C, 9A-9B, 10, and 11, reference characters 20, 100a, 100b) comprising a plurality of gas distribution slots. The spinneret assembly 44a contains a plurality of nozzles 236 through which the molten material is extruded into filaments 238. During extrusion the filaments 238 are contacted by gas (air) jets (not shown) disposed within a plurality of gas distribution slots within gas distribution plate 20a which draw the filaments 238.

In certain embodiments, each of the filaments 238 has an average diameter of less than about 10 microns. Desirably, each of the filaments 238 has an average diameter ranging from between about 1 micron to about 10 microns. More desirably, each of the filaments 238 has an average diameter ranging from between about 1 micron to about 9 microns.

In some embodiments, the spinneret assembly 44a may include a pair of cover strips 242, 242 which function to shelter the plurality of nozzles 236 from the entrained air in the room that may be drawn in from the sides and which could have a cooling effect on the extruded filaments 238.

The first polymer resin 222 can vary in composition and may be selected from those discussed previously. In one embodiment, the first polymer resin 222 can be a thermoplastic.

Still referring to FIG. 13, a second polymer resin 244, in the form of small solid pellets, granules or powder, is placed into a hopper 246 and is then routed through a conduit 248 to an extruder 250. In the extruder 250, the second polymer resin 244 is heated to an elevated temperature. The temperature will vary depending on the composition and melt temperature of a particular polymer. Usually, the second polymer resin 244 is heated to a temperature at or above its melting temperature. The melted, second polymer resin 244 is transformed into a molten material (polymer) which is then routed through a conduit filaments 252 to a spin beam 254 having a spinneret assembly 44b secured thereto. The spin beam 254 contains a plurality of nozzles 258 through which the molten material is extruder into filaments 260. Disposed downstream of the spinneret assembly 44b, the spin beam 254 comprises a gas distribution plate 20b having a plurality of gas distribution slots as previously discussed. The filaments 260 are contacted by gas (air) jets (not shown) within the gas distribution plate 44b, which draw the filaments 260.

In certain embodiments, each of the filaments has an average diameter of less than about 10 microns. Desirably, each of the filaments 260 has an average diameter ranging from between about 1 micron to about 10 microns. More desirably, each of the filaments 260 has an average diameter ranging from between about 1 micron to about 9 microns.

The spinneret assembly 44b may also includes a pair of cover strips 264, 264 which function to shelter the plurality of nozzles 258 from the entrained air in the room that may be drawn in from the sides and which could have a cooling effect on the extruded filaments 260.

The second polymer resin 244 can be identical to the first polymer resin filaments 222 or be different from the first polymer resin 222. The compositions of the first and second polymer resins, 22 and 44 respectively, will depend on the final composite nonwoven fabric 212 one wishes to produce. Likewise, the characteristics, such as diameter, tensile strength, etc. of the first filaments 238 can be identical to the characteristics of the second filaments 260 or be different therefrom. Generally, when the first and second polymer resins, 222 and 244 respectively, are the same, filaments will have the same diameter and strength. However, the first and second filaments 238, 260 could have different characteristics, such as diameter, strength, etc. if desired. In addition, the characteristics of the first and second filaments 238, 260 can be changed if the spinneret assemblies 44a, 44b, and the nozzles 236 and 258 have different physical dimensions, configurations and/or design. fibers, 40 and 62 respectively, to be identical, while in other applications, they can be different.

Still referring to FIG. 13, a stream of the fibers of the first material 214 is comingled between the streams of the first and second filaments, 238, 260 respectively. A majority of the fibers of the first material 214 will be positioned or sandwiched between the first and second first filaments, 238, 260 respectively, present in the first and second filament streams. In other words, a higher concentration of the fibers of the first material will be present in the middle portion of the finished, composite nonwoven fabric 212. The ratio of the fibers of the first material 214 to the ratio of the first and second filaments 238, 260 respectively, can vary.

It should be understood that the denier of the fibers of the first material 214, for example, absorbent staple/pulp fibers, can be greater than the denier of either the first or second filaments, 238, 260 respectively. By "denier" it is meant a unit of fineness for rayon, nylon and silk, based on a standard mass per length of 1 gram per 9,000 meters of yarn.

The first filaments 238 are formed from the first polymer resin 222 and the second filaments 260 are formed from the second polymer resin 44. The first polymer resin 222 can be identical to or be different from the second polymer resin 244. Each of the separate streams of the first and second filaments 238, 260 respectively, will join, merge or intersect with the steam of fibers of the first material 214.

The spin beams 232 and 254 are inclined at an angle theta Θ to the nozzle 220. This means that the separate streams of the first and second polymer filaments 238, 260, will contact the stream of the fibers of the first material 214 at an angle of inclination theta Θ. The angle of inclination theta Θ can range from between about 10° to about 75°. Desirably, the angle of inclination theta Θ can range from between about 30° to about 70°. More desirably, the angle of inclination theta Θ can range from between about 40° to about 65°. Even more desirably, the angle of inclination theta Θ can range from between about 40° to about 50°.

As discussed previously, spin beams 44a, 44b may be used to prepare filaments comprising monocomponent fibers or multicomponent fibers. In addition, the filaments may comprise blends of polymer or may comprise a single homopolymer. In some embodiments, the composite nonwoven fabric 212 may contain bicomponent fibers wherein the fibers have a sheath-core configuration with the core formed from one polymer and the surrounding sheath formed from a second polymer. Still another option is to produce the composite nonwoven fabric 212 from bicomponent fibers where the fibers have a side-by-side configuration. Those skilled in the polymer arts will be aware of various fiber designs incorporating two or more polymers.

In certain embodiments, the filaments may comprise bicomponent fibers having an eccentric or D-centric cross-section. Such filaments may comprise crimps that extend longitudinally along the length of the filaments. In some embodiments, the spin beam may include one or more polymer distribution plates that are configured to produce a nonwoven fabric comprising fibers having multiple cross-sections that are different from each other in a single layer.

Referring again to FIG. 13, the system and process 200 further includes depositing the comingled streams of fibers of the first material 214 and the first and second filaments, 238 and 260 respectively, onto a collection surface, such as a forming wire 266. The forming wire 266 can be constructed as a closed loop which travels around a plurality of rollers 268. Four spaced apart rollers 268, 268, 268 and 268 are shown in FIG. 13. One of the rollers 268 can be a drive roller which causes the forming wire 266 to move or rotate in a desired direction. In FIG. 12, the forming wire 266 is moving in a clockwise direction, see the arrows. The forming wire 266 has a foraminous surface 270 which contains a plurality of very small openings (not shown). Various kinds and types of forming wires 266 are commercially available today. Albany International Co. of Albany, N.Y. manufactures and sell a variety of such forming wires 266. Those skilled in the art of forming webs are knowledgeable about the various kinds and types of forming wires 266.

A vacuum source 272 is located beneath the forming wire 266. The vacuum source 272 can vary in design and construction. For example, the vacuum source 272 can be a vacuum box that is positioned directly below the point of contact of the comingling streams or be located slightly downstream from this point. The vacuum source 272 exerts a force on the various fibers of the first material 214 and the first and second filament 238 and 260 respectively, and supports the composite nonwoven fabric 212. The three streams will accumulate and the fibers forming the composite nonwoven fabric 212 will solidify and be advanced in the direction the forming wire 266 is moving. The composite nonwoven fabric 212 can then be wound up onto a wind-up spindle 274. At a predetermined length, the composite nonwoven fabric 212 can be severed or cut by a cutter 276. Various types of web cutter 276 are commercially available and are well known to those skilled in the art.

In some embodiments, additional layers may be added to the composite nonwoven fabric 212. For example, melt-blown, spunbond, or carded layers, for example, may be added to the composite nonwoven fabric. Further, one or more additional layers formed using a spin beam in accordance with those depicted in FIG. 1 or 2 may also be added to the composite nonwoven fabric. The system may also include multiple systems 200 depicted in FIG. 13.

In some embodiments, the composite nonwoven fabric may also be subject to a bonding step, such as mechanical bonding, thermal bonding, or chemical bonding. Processes and apparatus for bonding are discussed previously in connection with the system shown in FIG. 1.

As discussed previously, the composite nonwoven fabric 212 is particularly useful in the production of absorbent wipes. In certain embodiments, the composite nonwoven fabric 212 in accordance with embodiments of the invention may have a basis weight ranging from about 25 to 200 grams per square meter (gsm), and in particular, from about 35 to 100 gsm. In a preferred embodiment, the composite nonwoven fabric has a basis weight of about 40 to 60 gsm.

In some embodiments, the composite nonwoven fabric may comprise a solid additive comprising SAP. In such embodiments, the composite nonwoven fabric may have basis weights up to 300 gsm, such as a basis weight from 25 to 300 gsm, and in particular, from about 50 to 300 gsm.

Examples

In the following example, a series of gas flow simulations were performed to evaluate the performance of air flow through a gas distribution plate having a dumb-bell like shape (see, for example, FIG. 8D) and a tear drop/egg like shape (see, for example, FIG. 8H) in comparison to a gas distribution plate having a single filament nozzle concentrically surrounded by a gas outlet. The simulations were performed by Demcon Multiphysics of Enschede, The Netherlands.

The fluid flow of the gas distribution plates was simulated with the use of Computational Fluid Dynamics analysis in which virtual prototypes of the gas distribution plates were evaluated for velocity. The simulated gas flow velocity scale 500 indicating the relative simulated gas flow velocity based on color with a red color indicating slow to no gas flow and green to blue indicating relatively higher rates of gas flow through the gas distribution plate.

With reference to FIG. 14, a series of virtual gas flow velocity distribution plate are shown. Virtual gas flow velocity distribution plate A comprises a gas distribution plate in which individual nozzles were concentrically surrounded by a gas outlet. Virtual gas flow velocity distribution plate B comprised gas distribution slots having a dumb-bell like shape comprising two chambers, each comprising a filament nozzle, which are connected by a gas connecting channel. Virtual gas flow velocity distribution plate C comprised gas distribution slots having a tear drop like shape comprising two chambers, each comprising a filament nozzle in which the two chambers each include a pair of opposing edges that converge to connect the two chambers in a single gas distribution slot.

The flow velocity simulation of FIG. 14 was performed near the outlet of the gas distribution plate to analyze fluid flow as it is about to be discharged from the gas distribution plate and measures the velocity of the fluid as it moves vertically through the gas distribution plate.

Fluid flow having relatively high velocities are indicated by a green to blue color, with blue indicating higher fluid velocities, while red indicates low fluid velocities.

With respect to comparative virtual gas flow velocity distribution plate A, it can be seen that fluid flow between adjacent gas outlets is relatively slow or non-existent as indicated by the red color.

On the other hand, inventive virtual gas flow velocity distribution plate B shows a strong blue color in the fluid connecting channels disposed between adjacent chambers in a single gas distribution slot. These high velocities are desirable as they would help prevent adjacent extruded filaments from contacting each other as they are extruded. Contact of filaments may be undesirable because it can lead to roping and conglomeration of the filaments as they are extruded.

With respect to inventive virtual gas flow velocity distribution plate C, the velocities between adjacent chambers are not as high relative to inventive virtual gas flow velocity distribution plate B. However, for the most part they are solid green to green-blue, which may also provide improvements with respect to reducing roping and conglomeration of the filaments as they are extruded.

As may be noted by one skilled in the art, the simulated gas flow predicts improved airflow distribution and hence one could expect that the standard deviation of fiber size distribution is predictably lower yielding tighter fiber size distributions and the production of improved fabrics.

Modifications of the invention set forth herein will come to mind to one skilled in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for preparing a nonwoven fabric comprising:
   a first polymer source;
   a spin beam in fluid communication with the first polymer source, the spin beam including a spinneret assembly having a plurality of rows of filament nozzles that are arranged in an array, the filament nozzles being configured and arranged to extrude a plurality of filaments comprising a first polymer provided by the first polymer source;
   a gas distribution plate disposed downstream of the spinneret assembly, the gas distribution plate including a plurality of gas distribution slots that are each associated with one or more of the rows of the filaments nozzles;
   a gas source in fluid communication with the plurality of gas distribution slots such that a stream of gas is introduced into the plurality of gas distribution slots to draw and attenuate the filaments extruded by the plurality of filament nozzles; and
   a collection surface disposed downstream of the gas distribution plate for collecting the drawn and attenuated filaments thereon to form a nonwoven fabric, and wherein the gas distribution slots comprise a first chamber and a second chamber that are interconnected via a fluid channel, and wherein each chamber includes at least one filament nozzle disposed therein.

2. The system according to claim 1, wherein the plurality of gas distribution slots are configured and arranged to receive a corresponding row of filament nozzles of the spinneret assembly therein.

3. A system for preparing a nonwoven fabric comprising:
   a first polymer source;
   a spin beam in fluid communication with the first polymer source, the spin beam including a spinneret assembly having a plurality of rows of filament nozzles that are arranged in an array, the filament nozzles being configured and arranged to extrude a plurality of filaments comprising a first polymer provided by the first polymer source;
   a gas distribution plate disposed downstream of the spinneret assembly, the gas distribution plate including a plurality of gas distribution slots that are each associated with one or more of the rows of the filaments nozzles;

a gas source in fluid communication with the plurality of gas distribution slots such that a stream of gas is introduced into the plurality of gas distribution slots to draw and attenuate the filaments extruded by the plurality of filament nozzles; and a collection surface disposed downstream of the gas distribution plate for collecting the drawn and attenuated filaments thereon to form a nonwoven fabric, wherein the plurality of gas distribution slots are disposed adjacent to a corresponding row of filament nozzles, and wherein the spin beam comprises an alternating pattern of rows of filament nozzles and gas distribution slots.

4. The system according to claim 3, wherein each individual row of filament nozzles is disposed between two rows of gas distribution slots.

5. The system according to claim 1, wherein each chamber includes 1 to 4 filament nozzles disposed therein.

6. A system for preparing a nonwoven fabric comprising:
a first polymer source;
a spin beam in fluid communication with the first polymer source, the spin beam including a spinneret assembly having a plurality of rows of filament nozzles that are arranged in an array, the filament nozzles being configured and arranged to extrude a plurality of filaments comprising a first polymer provided by the first polymer source;
a gas distribution plate disposed downstream of the spinneret assembly, the gas distribution plate including a plurality of gas distribution slots that are each associated with one or more of the rows of the filaments nozzles;
a gas source in fluid communication with the plurality of gas distribution slots such that a stream of gas is introduced into the plurality of gas distribution slots to draw and attenuate the filaments extruded by the plurality of filament nozzles; and
a collection surface disposed downstream of the gas distribution plate for collecting the drawn and attenuated filaments thereon to form a nonwoven fabric,
wherein the gas distribution slots comprise a plurality of successive chambers arranged in a row and wherein a fluid connecting channel provides fluid communication between adjacent chambers.

7. A system for preparing a nonwoven fabric comprising:
a first polymer source;
a spin beam in fluid communication with the first polymer source, the spin beam including a spinneret assembly having a plurality of rows of filament nozzles that are arranged in an array, the filament nozzles being configured and arranged to extrude a plurality of filaments comprising a first polymer provided by the first polymer source;
a gas distribution plate disposed downstream of the spinneret assembly, the gas distribution plate including a plurality of gas distribution slots that are each associated with one or more of the rows of the filaments nozzles;
a gas source in fluid communication with the plurality of gas distribution slots such that a stream of gas is introduced into the plurality of gas distribution slots to draw and attenuate the filaments extruded by the plurality of filament nozzles; and
a collection surface disposed downstream of the gas distribution plate for collecting the drawn and attenuated filaments thereon to form a nonwoven fabric,
wherein the gas distribution slot comprises a pair of converging first and second chambers wherein each chamber comprising a central chamber and a pair of opposing sides that extend from peripheral edges of the central chamber and that converge towards a central point disposed between the first and second chambers.

8. The system according to claim 1, wherein the plurality of gas distribution slots extend in a cross direction of the spin beam.

9. The system according to claim 1, wherein the plurality of filament nozzles extend at least partially through a thickness of the gas distribution plate.

10. The system according to claim 1, wherein the gas distribution slots have a pair of opposing side walls extending along a length of each of the gas distribution slots, and wherein the rows of filament nozzles are disposed between the pair of opposing side walls.

11. The system according to claim 10, wherein an angle formed between the opposing sidewalls and sidewalls of the filament nozzles is from 0° to 60°.

12. The system according to claim 1, further comprising a second polymer source for providing a second polymer to the spin beam, wherein the spin beam is configured and arranged to produce multicomponent filaments.

13. The system according to claim 12, wherein the multicomponent filaments are bicomponent filaments.

14. The system according to claim 1, further comprising a source of solid additives, wherein the solid additives are introduced into a stream of plurality of filaments extruded from the spin beam prior to collection of the filaments on the collection surface.

15. The system according to claim 14, wherein the source of solid additives comprises cellulose pulps, natural fibers, or a combination thereof.

16. The system according to claim 14, wherein the source of solid additives comprises a super absorbent polymer.

17. A method for preparing a nonwoven fabric comprising:
providing a first polymer source;
introducing a first polymer from said first polymer source into a spin beam in fluid communication with the first polymer source, the spin beam including a spinneret assembly having a plurality of rows of filament nozzles that are arranged in an array and
a gas distribution plate disposed downstream of the spinneret assembly, the gas distribution plate including a plurality of gas distribution slots that are each associated with one or more of the rows of the filaments nozzles;
extruding a plurality of filaments comprising the first polymer provided by the first polymer source;
surrounding the filament nozzles and the extruded plurality of filaments with a stream of gas that is introduced into the plurality of gas distribution slots;
drawing and attenuating the plurality of filaments extruded by the plurality of filament nozzles; and
depositing the plurality filament nozzles onto a collection surface disposed downstream of the gas distribution plate to form a nonwoven fabric web, and wherein the gas distribution slots comprise a first chamber and a second chamber that are interconnected via a fluid channel, and wherein each chamber includes at least one filament nozzle disposed therein.

18. The method of claim 17, further comprising introducing a stream of solid additives into the plurality of filaments prior to the plurality of filaments being deposited onto the collection on surface.

19. The method of claim 17, wherein the solid additives comprise cellulose pulps, natural fibers, or a combination thereof.

\* \* \* \* \*